United States Patent
Kubba et al.

(10) Patent No.: US 9,757,056 B1
(45) Date of Patent: Sep. 12, 2017

(54) OVER-MOLDING OF SENSOR APPARATUS IN EYE-MOUNTABLE DEVICE

(71) Applicant: Verily Life Sciences LLC, Mountain View, CA (US)

(72) Inventors: Michael Kubba, Mountain View, CA (US); Jeffrey George Linhardt, Pleasanton, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1071 days.

(21) Appl. No.: 13/661,735

(22) Filed: Oct. 26, 2012

(51) Int. Cl.
*A61B 5/05* (2006.01)
*A61B 5/145* (2006.01)
*A61B 5/00* (2006.01)

(52) U.S. Cl.
CPC ........ *A61B 5/14532* (2013.01); *A61B 5/6821* (2013.01)

(58) Field of Classification Search
CPC .... A61B 5/1486; A61B 5/6821; C12Q 1/006; G01N 27/3272; H01L 31/048; H01L 31/0516; H01L 31/0682; G02C 7/04; G02C 7/041; G02C 7/12; G02C 7/049; G02C 2202/16; G02C 2202/20; Y02E 10/547; G02B 1/04; G02B 1/043; A61F 2/145; A61F 2/1648; B29D 11/00048
See application file for complete search history.

(56) References Cited

U.S. PATENT DOCUMENTS 3,958,560 A 5/1976 March
4,014,321 A 3/1977 March
(Continued)

FOREIGN PATENT DOCUMENTS

EP 0369942 5/1990
EP 0686372 12/1995
(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
(Continued)

*Primary Examiner* — Navin Natnithithadha
*Assistant Examiner* — Eric Messersmith
(74) *Attorney, Agent, or Firm* — McDonnell Boehnen Hulbert & Berghoff LLP

(57) ABSTRACT

Example eye-mountable devices and methods for fabricating eye-mountable devices are described. A method may involve forming a first polymer layer, which defines an anterior side of the eye-mountable device and is configured to allow an analyte to diffuse therethrough. Further, the method may involve positioning a sensor apparatus on the first polymer layer, wherein the sensor apparatus comprises at least one sensor configured to detect the analyte, and wherein the at least one sensor is oriented relative to the first polymer layer to receive the analyte via diffusion through the first polymer layer. The sensor apparatus may have a height dimension of at least 50 micrometers. Still further, the method may involve forming a second polymer layer over the first polymer layer and the sensor apparatus, such that the sensor apparatus is fully enclosed by the first polymer layer and the second polymer layer.

15 Claims, 12 Drawing Sheets

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,135,592 A * | 8/1992 | Melvin ............ A61F 2/1648 156/73.1 |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,579,918 B1 * | 6/2003 | Auten ................ A61F 2/145 351/159.33 |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |

(56) References Cited

U.S. PATENT DOCUMENTS

| | | |
|---|---|---|
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder et al. |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Bionic contact lens 'to project emails before eyes,' http://www.kurzweilai.netforums/topic/bionic-contact-lens-to-project-emails-before-eyes, Last accessed Mar. 14, 2012, 2 pages.

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011, http://www.econonnist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-μW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-μW Wirelessly Powered CMOS Glucose Sensor for an Active Contact Lens," 2011 IEEE International Solid-State Circuits Conference, Session 2, Feb. 21, 2011, 3 pages.

Lingley, et al., "A Single-Pixel Wireless Contact Lens Display," Journal of Micromechanics and Microengineering, 2011, pp. 1-8.

Lingley, et al., "Multipurpose integrated active contact lenses," SPIE, 2009, 2 pages.

Liu, et al., "Miniature Amperometric Self-Powered Continuous Glucose Sensor with Linear Response," Analytical Chemistry, 2012, 7 pages.

Loncar, et al., "Design and Fabrication of Silicon Photonic Crystal Optical Waveguides," Journal of Lightwave Technology, Oct. 2000, pp. 1402-1411, vol. 18, No. 10.

(56) References Cited

OTHER PUBLICATIONS

Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions on Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh, et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.

\* cited by examiner

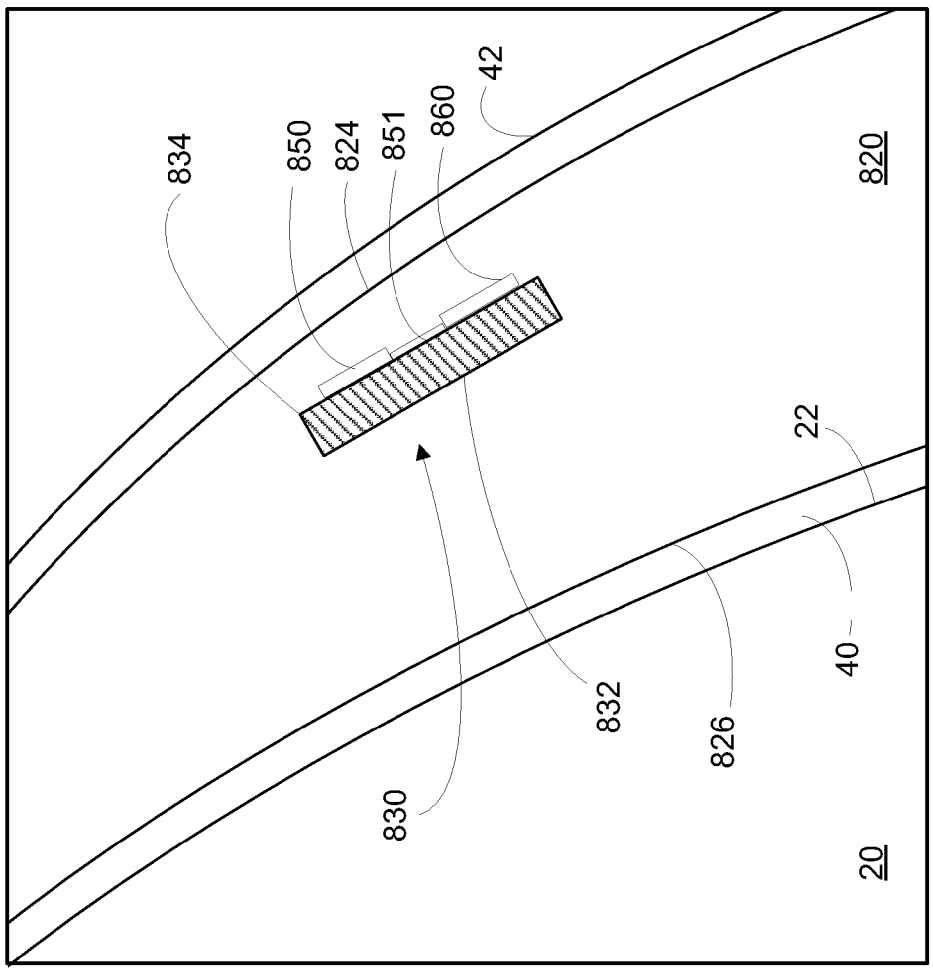
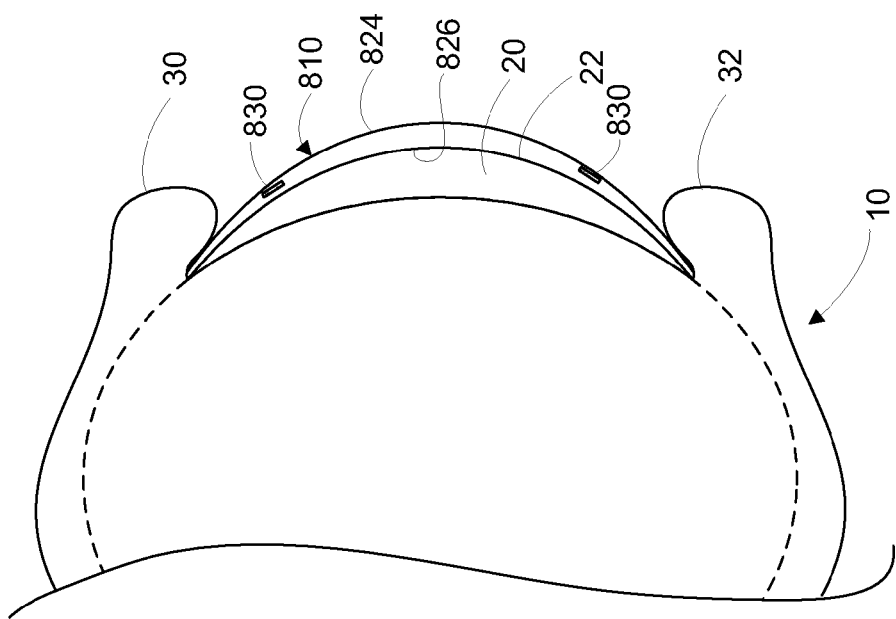

OVER-MOLDING OF SENSOR APPARATUS IN EYE-MOUNTABLE DEVICE

BACKGROUND

Unless otherwise indicated herein, the materials described in this section are not prior art to the claims in this application and are not admitted to be prior art by inclusion in this section.

An eye-mountable device may be configured to monitor health-related information based on at least one analyte detected from an eye of a user wearing the eye-mountable device. Such an eye-mountable device may include a sensor apparatus configured to detect at least one analyte (e.g., glucose). For example, the eye-mountable device may be in the form of a contact lens that includes a sensor apparatus configured to detect the at least one analyte. The sensor apparatus may monitor health-related information of a user of the eye-mountable device, such as glucose level of the user. Further, the sensor apparatus may monitor various other types of health-related information.

SUMMARY

In one aspect, an example method for fabricating an eye-mountable device involves: (i) forming a first polymer layer, wherein the first polymer layer defines an anterior side of the eye-mountable device and is configured to allow an analyte to diffuse therethrough; (ii) positioning a sensor apparatus on the first polymer layer, wherein the sensor apparatus comprises at least one sensor configured to detect the analyte, and wherein the at least one sensor is oriented relative to the first polymer layer to receive the analyte via diffusion through the first polymer layer, wherein the sensor apparatus has a height dimension of at least 50 micrometers; and (iii) forming a second polymer layer over the first polymer layer and the sensor apparatus, such that the sensor apparatus is fully enclosed by the first polymer layer and the second polymer layer, wherein the second polymer layer defines a posterior side of the eye-mountable device.

In another aspect, an example method for fabricating an eye-mountable device involves: (i) forming a first polymer layer, wherein the first polymer layer defines an anterior side of the eye-mountable device and is configured to allow an analyte to diffuse therethrough, and wherein the first polymer layer comprises at least one interlocking feature; (ii) positioning a sensor apparatus on the first polymer layer, wherein positioning the sensor apparatus on the first polymer layer comprises aligning the sensor apparatus with the at least one interlocking feature on the first polymer layer, wherein the sensor apparatus comprises at least one sensor configured to detect the analyte, and wherein the at least one sensor is oriented relative to the first polymer layer to receive the analyte via diffusion through the first polymer layer; and (iii) forming a second polymer layer over the first polymer layer and the sensor apparatus, such that the sensor apparatus is fully enclosed by the first polymer layer and the second polymer layer, wherein the second polymer layer defines a posterior side of the eye-mountable device, and wherein the second polymer layer comprises at least one corresponding interlocking feature, wherein each corresponding interlocking feature corresponds with a respective interlocking feature of the first polymer layer.

In yet another aspect, an eye-mountable device is disclosed. An example eye-mountable device includes: (i) a first polymer layer, wherein the first polymer layer defines an anterior side of the eye-mountable device and is configured to allow an analyte to diffuse therethrough, and wherein the first polymer layer comprises at least one interlocking feature; (ii) a second polymer layer wherein the second polymer layer defines a posterior side of the eye-mountable device, and wherein the second polymer layer comprises at least one corresponding interlocking feature, wherein each corresponding interlocking feature corresponds with a respective interlocking feature of the first polymer layer; and (iii) a sensor apparatus, wherein the sensor apparatus is fully enclosed by the first polymer layer and the second polymer layer, wherein the sensor apparatus comprises at least one sensor configured to detect the analyte, and wherein the at least one sensor is oriented relative to the first polymer layer to receive the analyte via diffusion through the first polymer layer.

In still yet another aspect, an example method for fabricating an eye-mountable device involves: (i) forming a first polymer layer, wherein the first polymer layer defines a posterior side of the eye-mountable device; (ii) positioning a sensor apparatus on the first polymer layer; and (iii) forming a second polymer layer over the first polymer layer and the sensor apparatus, such that the sensor apparatus is fully enclosed by the first polymer layer and the second polymer layer, wherein the second polymer layer defines an anterior side of the eye-mountable device and is configured to allow an analyte to diffuse therethrough, wherein the sensor apparatus comprises at least one sensor configured to detect the analyte, and wherein the at least one sensor is oriented relative to the second polymer layer to receive the analyte via diffusion through the second polymer layer, and wherein the sensor apparatus has a height dimension of at least 50 micrometers.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 8b is an aspect view of the example eye-mountable device shown in FIG. 8a.

FIG. 8c is a side cross-section view of the example eye-mountable device of FIGS. 8a and 8b while mounted to a corneal surface of an eye, according to an example embodiment.

FIG. 8d is a side cross-section view showing the tear film layers surrounding the surfaces of the example eye-mountable device mounted as shown in FIG. 8c, according to an example embodiment.

DETAILED DESCRIPTION

Figure 1:
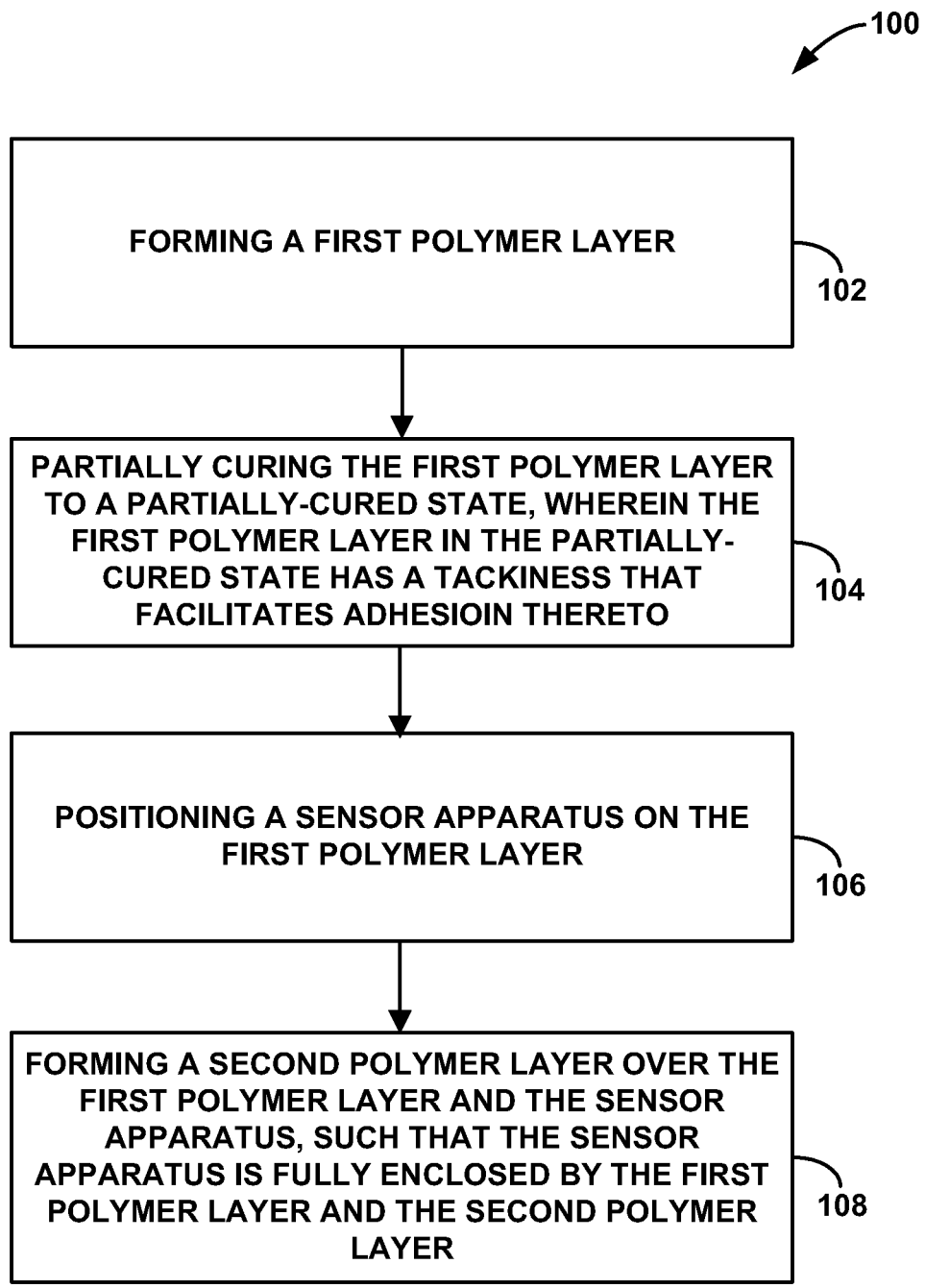
FIG. 1 is a flow chart illustrating a method according to an example embodiment.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. OVERVIEW

An eye-mountable device may be configured to monitor health-related information based on at least one analyte detected from an eye of a user wearing the eye-mountable device. Such an eye-mountable device may include a sensor apparatus configured to detect the at least one analyte.

A sensor apparatus disposed in an eye-mountable device may include materials that may cause discomfort to a user if the materials are in direct contact with an eye of the user. Thus, in some situations, it may be beneficial for an eye-mountable device having such a sensor apparatus to be configured such that the sensor apparatus is fully enclosed by eye-compatible material, such as polymer material. Further, in some situations, it may be beneficial for the eye-compatible material disposed over the sensor apparatus to have a well-defined thickness, such that the eye-compatible layer may allow for diffusion of an analyte to facilitate the monitoring of health-related information. In some cases, a thinner polymer layer may allow for more diffusion of analyte than a thicker polymer layer. For example, a polymer layer having a thickness of 50 micrometers or less may allow for more diffusion of a given analyte (e.g., glucose) than a polymer layer having a thickness of 100 micrometers or more.

The methods and systems described herein can facilitate fabrication of an eye-mountable device, where the eye-mountable device has a thin polymer layer of a well-defined thickness (e.g., less than 50 micrometers). A sensor may then be oriented relative to the thin polymer layer to receive the analyte via diffusion through the thin polymer layer and/or pores formed in the thin polymer layer. An example fabrication method may involve forming a first polymer layer, wherein the first polymer layer defines an anterior side of the eye-mountable device and is configured to allow an analyte to diffuse therethrough. Further, the example fabrication method may then involve positioning a sensor apparatus on the first polymer layer, wherein the sensor apparatus comprises at least one sensor configured to detect the analyte, and wherein the at least one sensor is oriented relative to the first polymer layer to receive the analyte via diffusion through the first polymer layer, wherein the sensor apparatus has a height dimension of at least 50 micrometers. Still further, the example fabrication method may then involve forming a second polymer layer over the first polymer layer and the sensor apparatus, such that the sensor apparatus is fully enclosed by the first polymer layer and the second polymer layer, wherein the second polymer layer defines a posterior side of the eye-mountable device.

As used throughout this disclosure, the anterior side of the eye-mountable device refers to the outward-facing side of the eye-mountable device, whereas the posterior side of the eye-mountable device refers to the inward-facing side of the eye-mountable device. In particular, when the eye-mountable device is mounted on an eye of the user, the anterior side corresponds to the side of the eye-mountable device that is facing outward and thus not touching the eye of the user. Further, when the eye-mountable device is mounted on an eye of the user, the posterior side corresponds to the side of the eye-mountable device that is facing inward and thus touching the eye of the user.

When fabricating such an eye-mountable device, precise placement of the sensor apparatus in the surrounding polymer layers may be desired. For instance, it may be desirable for the sensor apparatus to be placed on or near the periphery of the eye-mountable device, so as to limit interference with the user's field of view when the device is mounted on an eye of the user. Beneficially, the disclosed methods and systems allow for placement of the sensor apparatus in a desired position relative to the surrounding polymer layers.

Further, during fabrication of an eye-mountable device, it may be desirable for the sensor apparatus to remain in a fixed position during fabrication of the eye-mountable device. For instance, movement of the sensor apparatus during the formation of the second layer may result in improper placement of the sensor apparatus relative to the surrounding polymer layers. Therefore, in an example, forming the first polymer layer may involve partially curing the first polymer layer to a partially-cured state. In the partially-cured state, the first polymer layer has a tackiness that facilitates adhesion thereto, and the sensor apparatus may be placed on this partially-cured polymer layer. In this way, the sensor apparatus may remain adhered to the first polymer layer in a secure location during subsequent formation steps.

In another example, the first polymer layer may include at least one interlocking feature, and positioning the sensor apparatus on the first polymer layer may involve aligning the sensor apparatus with the at least one interlocking feature on the first polymer layer. Beneficially, in this way, the sensor apparatus may remain secured to the first polymer layer during subsequent formation steps. In yet another example, an adhesive may be applied to the sensor apparatus and/or first polymer layer before the sensor apparatus is placed on the first polymer layer. This applied adhesive may facilitate adhesion of the sensor apparatus to the first polymer layer.

II. EXAMPLE METHODS

Example methods for fabricating an eye-mountable device are disclosed. FIG. 1 is a flow chart illustrating a method according to an example embodiment. More specifically, example method 100 involves forming a first polymer layer, as shown by block 102. The method may then involve partially curing the first polymer layer to a partially-cured state, wherein the first polymer layer in the partially-cured state has a tackiness that facilitates adhesion thereto, as shown by block 104. Further, the method may then involve positioning a sensor apparatus on the first polymer layer, as shown by block 106. The method may then involve forming a second polymer layer over the first polymer layer and the sensor apparatus, such that the sensor apparatus is fully enclosed by the first polymer layer and the second polymer layer, as shown by block 108.

For purposes of illustration, method 100 is described below as being carried out by a fabrication device that utilizes cast or compression molding. It should be understood, however, that method 100 may be carried out by a fabrication device that utilizes other methods for forming the polymer layers.

A. Forming a First Polymer Layer

As mentioned above, at block 102 the fabrication device may form a first polymer layer. The fabrication device may include molding cavities, such as molding cavities that are suitable for cast molding. FIG. 2 illustrates an example fabrication device that includes example molding cavities that may be used to form the first polymer layer. In particular, FIG. 2 illustrates a fabrication device 200 that includes a first molding cavity 202 and a second molding cavity 204. This first molding cavity 202 may be filled with polymer material 206, and the polymer material 206 may be compressed into the first layer 208 by second molding cavity 204.

First polymer layer 208 may be formed with a thickness that allows an analyte to diffuse therethrough. The first and second cast molding cavities may be configured to achieve a given desired thickness of the first polymer layer 208. For instance, in an example, the first polymer layer has a thickness of less than 50 micrometers. Typically, as a polymer layer becomes thicker, the polymer layer allows for less diffusion through the layer. As an example, diffusion of a given analyte is typically greater through a 25 micrometer polymer layer than through a 100 micrometer or thicker polymer layer. For at least some types of analyte, a polymer layer having a thickness of less than 50 micrometers can allow for a sufficient amount of analyte to diffuse therethrough in order for the eye-mountable device to perform health-related measurements. In general, however, the thickness of the polymer layer through which the analyte diffuses to reach the sensor for measurement can be selected based on the type of analyte, the type of polymer, the type of sensor, and/or other considerations.

In accordance with an example embodiment, the thickness of the first polymer layer 208 may be selected based on the particular analyte or analytes the eye-mountable device is configured to detect. For example, an optimal thickness for a first analyte may be 10 micrometers, while an optimal thickness for a second analyte may be 25 micrometers. Other examples are possible as well.

Figure 2A:
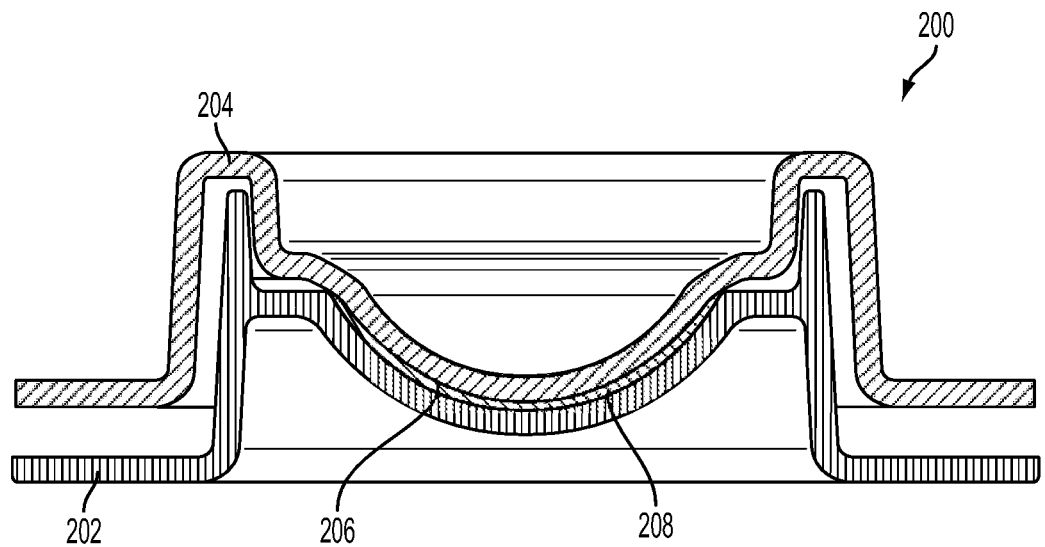
FIG. 2a is an illustration of formation of a first polymer layer, according to an example embodiment.
Figure 2B:
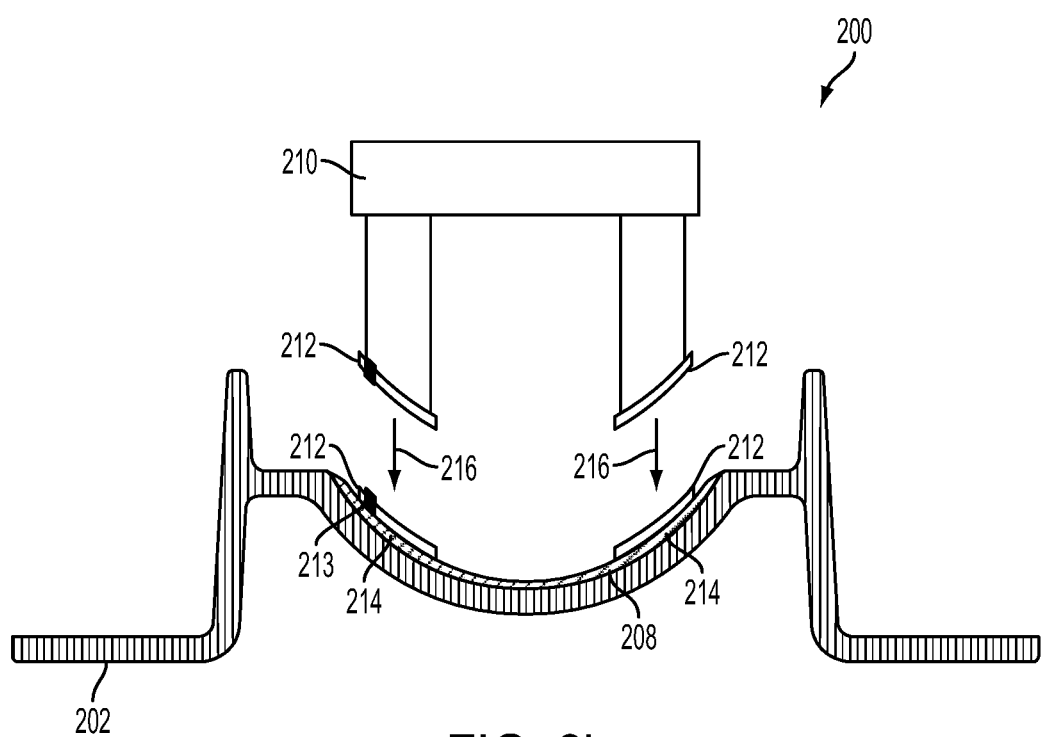
FIG. 2b is an illustration of positioning of a sensor apparatus on the first polymer layer, according to an example embodiment.

Returning to FIG. 2a, this first polymer layer 208 will define an anterior side of the eye-mountable device. That is, the first polymer layer 208 will define an outer edge of the eye-mountable device. FIG. 2d is an illustration of the eye-mountable device 230 after completely formed. When mounted on an eye of a user, the anterior side of the eye-mountable device 230 defined by the first polymer layer 208 corresponds to the side of the device not touching the eye of the user. First molding cavity 202 may be shaped so as to define the shape of the anterior side of the eye-mountable device. For example, the curvature of the anterior side may be defined by the first molding cavity 202.

Further, the molding cavities 202, 204 may be configured to control the thickness of the first polymer layer 208 formed between the molding cavities 202, 204. For example, the first molding cavity 202 and the second molding cavity 204 may be designed so as to allow for a layer having a 10 micrometer thickness between the two cavities. As such, when the two molding cavities are pressed together during the formation of the first polymer layer 208, the resulting polymer layer 208 will have a thickness of around 10 micrometers.

In accordance with an example embodiment, the polymer material 206 may be any material that can form an eye-compatible polymer layer. For example, the polymer material 206 may be a formulation containing polymerizable monomers, such as hydrogels, silicone hydrogels, silicone elastomers, and rigid gas permeable materials. Further, this polymer material 206 may form a transparent or substantially transparent polymer layer. As such, the use of polymer material 206 may result in an eye-mountable device 230 through which the wearer can see when mounted on the wearer's eye. In an example, the polymer material 206 is a hydrogel material, such as silicone hydrogel. As known in the art, hydrogel materials are commonly used in contact-lens technology and are well-suited for eye-mountable devices. Other materials are possible as well.

In an example, the molding cavities may be configured so as to allow sufficient pinch off to provide for suitable edges for the eye-mountable device.

As mentioned above, although FIG. 2a illustrates forming the first polymer layer 208 through cast molding, other methods for forming the first polymer layer 208 are possible as well. For example, the first polymer layer 208 may be formed via injection molding. In injection molding, rather than the polymer material being compressed between molding cavities, molding material may heated and injected or otherwise forced into a molding cavity or cavities. The injected molding material may then cool and harden to the configuration of the molding cavity or cavities.

As another example, the first polymer layer 208 may be formed via spin casting. Through spin-casting techniques, the fabrication device may form a first polymer layer of a precise thickness. In an example, a spin-casting mold may be spun along its central access at a set speed, and the polymer may be introduced to the mold as the mold is spinning in order to form the first polymer layer. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

B. Partially Curing the First Polymer Layer to a Partially-Cured State

After forming the first polymer layer 208, the fabrication device 200 may partially cure the first polymer layer. Curing involves the hardening of a polymer material by cross-linking of polymer chains, and curing may be, for example, brought about by chemical additives, ultraviolet radiation, electron beam, and/or heat. In an example, polymer material 206 may be light-curable polymer material, and the fabrication device 200 may be configured to cure the light-curable polymer material 206 using light, such as ultraviolet (UV) light or visible light.

The polymer layer 208 may be cured to a partially-cured state. In an example, this may involve curing the material to a partially-cured state that is approximately 50-75% of a fully cured state. Other partially-cured states are possible as well. Beneficially, by partially curing the first polymer layer to a partially-cured state, the first polymer layer 208 may have a tackiness that facilitates adhesion thereto. As described in more detail below, this tackiness may ensure that a sensor apparatus placed on the first polymer layer 208 remains securely fixed in a given location throughout the formation of the eye-mountable device 230.

The tackiness exhibited by the partially-cured polymer layer 208 may be different for different polymers. Accordingly, the fabrication device 200 may be cure different polymer materials differently than other polymer materials (e.g., a first polymer material may be cured more than a second polymer material). Further, in addition to light curing, other methods of curing are possible as well, such as chemical additives and/or heat. Yet still further, in other example embodiments, the first polymer layer 208 may be completely cured. Alternatively, the fabrication device 200 may bypass the curing process at this stage.

C. Positioning a Sensor Apparatus on the First Polymer Layer

After partially curing the first polymer layer 208 to a partially-cured state, the fabrication device 200 may position a sensor apparatus on the first polymer layer 200, as shown by block 106. The fabrication device 200 may include a positioning apparatus that is configured to position the sensor apparatus on the first polymer layer. FIG. 2b illustrates an example positioning of the sensor apparatus on the first polymer layer. As shown in FIG. 2b, the fabrication device 200 includes a positioning apparatus 210 that positions a sensor apparatus 212 at a desired location on the first polymer layer 208.

In an example, the sensor apparatus 212 comprises at least one sensor and a ring-shaped support, where the at least one sensor of the sensor apparatus is mounted on the ring-shaped support. In this case, positioning the sensor apparatus 212 on the first polymer layer 208 may include positioning the ring-shaped support on first polymer layer 208. The ring-shaped support may be placed on the periphery of the eye-mountable device 230, so as to limit interference with the user's field of view when the eye-mountable device 230 is mounted on an eye of the user. Further, the ring-shaped support of the sensor apparatus 212 may be more rigid than the first and second polymer layers.

In order to position the sensor apparatus 212, the fabrication device 200 may remove the second molding cavity 204, and the positioning system 210 may then place the sensor apparatus 212 at a given location 214 on the first polymer layer. The sensor apparatus 212 may include at least one sensor 213 configured to detect an analyte. The positioning system 210 may position the sensor apparatus 212 such that the at least one sensor 213 is oriented relative to the first polymer layer 208 to receive the analyte via diffusion through the first polymer layer 208. In other words, the at least one sensor 213 may be oriented to directly face the first polymer layer 208.

In an example, the positioning apparatus 210 may be a robotic system configured to place the sensor apparatus 212 at the defined location 214 on the first polymer layer 208. For instance, the robotic system may (i) pick up the sensor apparatus 212 (e.g., via suction), (ii) position the sensor apparatus 212 above the first polymer layer 208, and then (iii) lower the sensor apparatus 212 toward the first polymer layer 208, as shown by arrows 216. When the sensor apparatus 212 is positioned in the desired location 214 on the first polymer layer 208, the positioning apparatus 210 may then release the sensor apparatus 212 (e.g., by releasing the suction).

In an example, the positioning apparatus 210 may include a vision system configured to assist with the placement of the sensor apparatus 212. Such a vision system may facilitate guiding the sensor apparatus 212 to a precise location on the first polymer layer 208. In an example, a vision system may be appropriate for situations in which the production specifications for the eye-mountable device have requirements with very low tolerances related to the positioning of the sensor apparatus within the eye-mountable device.

Since the polymer layer 208 is in a partially cured state, the sensor apparatus 212 may adhere to the first polymer layer in the fixed location 214. Beneficially, this adhesion may allow the sensor apparatus 212 to remain fixed or substantially fixed in that location 214 during subsequent formation steps. In some situations, such as for large-scale production purposes, it may be desirable to not only place the sensor apparatus 212 at a precise location 214, but it may also be desirable to repeatedly place and maintain the sensor apparatus at this precise location for a plurality of eye-mountable devices. Beneficially, fabrication of an eye-mountable device in accordance with the exemplary embodiment allows for such repeatable and precise placement.

FIG. 2b illustrates placement of the sensor apparatus 212 at a precise location 214 in an XYZ plane on the first polymer layer 208. In addition to precise placement of the sensor apparatus 212 in an XYZ plane, the positioning system 210 may also be configured to place the sensor apparatus 212 in a desired rotational orientation.

As mentioned above, the sensor apparatus 212 may comprise a ring-shaped support, where the at least one sensor 213 is mounted on the ring-shaped support. In such an example, the at least one sensor 213 may be mounted at a particular angle along the circumference of the ring-shaped support. In some implementations, it may be desirable position the ring-shaped support such that the sensor 213 is at a given rotational location within the eye-mountable device 230. For example, it may be desirable for the at least one sensor 213 to be located on a bottom portion of the eye-mountable device 230, so that when a user is wearing the eye-mountable device 230, the at least one sensor 213 rests at the six o'clock position of the eye-mountable device rather than the 12 o'clock position of the eye-mountable device.

Although the sensor apparatus 212 may comprise at least one sensor mounted on a ring-shaped support, in other embodiments, the at least one sensor may stand alone.

The sensor apparatus 212 may vary in size. For instance, the sensor apparatus may vary in size depending on which analyte the eye-mountable device is configured to detect. In an example, the sensor apparatus 212 is a substrate shaped as a ring with approximately a 1 centimeter diameter, a radial thickness of approximately 1 millimeter, and a maximum height of approximately 50 to 150 micrometers. Of course, other sizes of the sensor apparatus 212 are possible as well.

In an example, the sensor apparatus has a height dimension of at least 50 micrometers. In other words, at some point of the sensor apparatus, the height of the sensor apparatus may be at least 50 micrometers. In an example, this height dimension may correspond to the maximum height of the sensor apparatus. In accordance with the present disclosure, the maximum height of the sensor apparatus 212 corresponds to the height of the sensor apparatus 212 at its highest point. For instance, in the example where the sensor apparatus comprises at least one sensor mounted on a ring-shaped support, the height of the sensor apparatus 212 may vary (and thus the sensor apparatus 212 may have various height dimensions). For example, the height of the sensor apparatus 212 may be higher at a point where the at least one sensor 213 is mounted on the ring-shaped support, whereas the height may be lower at a point where there is no sensor on the ring shaped-support. In such an example, the maximum height may correspond to the point where the at least one sensor 213 is mounted on the ring-shaped support.

In yet another example, an adhesive may be applied to the sensor apparatus and/or first polymer layer before the sensor apparatus is placed on the first polymer layer. This applied adhesive may facilitate adhesion of the sensor apparatus to the first polymer layer. For instance, a small amount of adhesive may be applied to a fully cured first polymer layer, and the sensor apparatus may be positioned on this small amount of adhesive such that the sensor apparatus adheres to the first polymer layer. Additionally or alternatively, a small amount of adhesive may be applied to the sensor apparatus, and the sensor apparatus may then be placed on the first polymer layer (e.g., a fully cured first polymer layer) such that the sensor apparatus adheres to the first polymer layer.

D. Forming a Second Polymer Layer over the First Polymer Layer and the Sensor Apparatus As mentioned above, at block 108, the fabrication device may form a second polymer layer over the first polymer layer and the sensor apparatus, such that the sensor apparatus is fully enclosed by the first polymer layer and the second polymer layer. This second polymer layer may define a posterior side of the eye-mountable device.

Figure 2C:
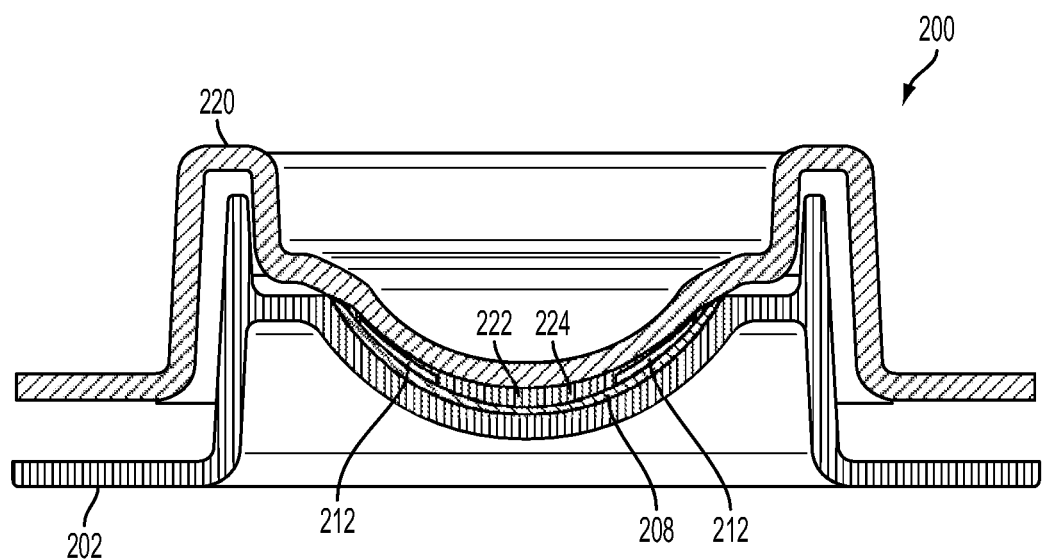
FIG. 2c is an illustration of formation of a second polymer layer over the first polymer layer and the sensor apparatus, according to an example embodiment.
Figure 2D:
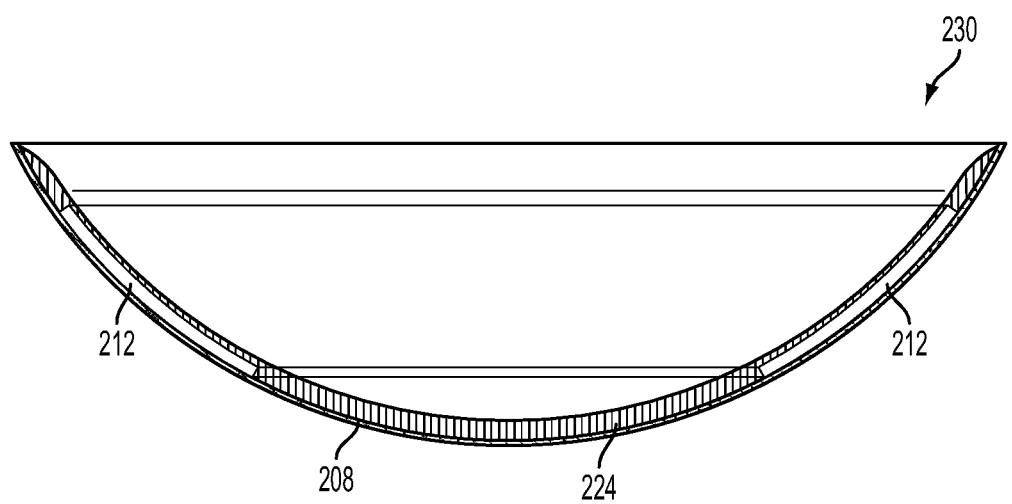
FIG. 2d is an illustration of an example eye-mountable device, according to an example embodiment.

FIG. 2c illustrates the formation of the second polymer layer. In particular, FIG. 2c illustrates an example third molding cavity 220. Third molding cavity 220 may define the posterior side of the eye-mountable device. In particular, the curvature of the posterior side may be defined by the third molding cavity 220. Further, the molding cavities 202, 220 may be configured to control the thickness of the layer formed between the two cavities. For example, the first molding cavity 202 and the third molding cavity 220 may be designed so as to define the final thickness of the eye-mountable device 230.

With reference to FIG. 2c, this first molding cavity 202, which already holds the first polymer layer 208 to which sensor apparatus 212 is adhered, may be filled with the polymer material 222. This polymer material 222 may be formed into second polymer layer 224 by the compression between first molding cavity 202 and third molding cavity 220. As a result, second polymer layer 224 may over-mold the sensor apparatus 212, such that the sensor apparatus 212 is fully enclosed by the first polymer layer 208 and the second polymer layer 224.

In an example, the second polymer layer 224 is thicker than the first polymer layer 208. For example, the second polymer layer 208 may have a maximum thickness between 100 and 500 micrometers. It should be understood that since the second polymer layer 224 over-molds the sensor apparatus 212, the second polymer layer 224 may not have a uniform thickness. For instance, the thickness of the second polymer layer 224 above the sensor apparatus 212 may be less than the thickness of the second polymer layer 212 that is not touching the sensor apparatus 212, as shown in FIG. 2c.

After the second polymer layer 224 is formed, the fabrication device 200 may cure the eye-mountable device 230, so as to fully cure both the first polymer layer 208 and the second polymer layer 224. FIG. 2d depicts a perspective cross-section of eye-mountable device 230 after the device 230 is removed from the fabrication device 200 and after the sensor apparatus 212 is fully enclosed by the first polymer layer 208 and the second polymer layer 212.

As is clear from FIG. 2d, the anterior side defined by the first polymer layer 208 is a thin layer, while the second polymer layer 224 is a thicker layer. In accordance with an example, the maximum thickness of the final device may range from 100-500 micrometers. Further, in such an example, the thin first polymer layer 208 may be less than 50 micrometers, while the thicker second polymer layer 224 may have a maximum thickness of between 100 and 500. In other examples, the first polymer layer and second polymer layer may each have a larger or smaller thickness.

In an example, the second polymer layer 224 may be composed of the same polymer material as the first polymer layer 208. However, in other examples, the second polymer layer may be composed of a different polymer material than the first polymer layer.

In the above example described with respect to method 100, the first polymer layer formed defines the anterior side of the eye-mountable device and the second polymer layer formed defines the posterior side of the eye-mountable device. However, in another example of the disclosed method, forming the first polymer layer may involve forming the first polymer layer such that the first polymer layer defines the posterior side of the eye-mountable device, and forming the second polymer layer may involve forming the second polymer layer such that the second polymer layer defines the anterior side of the eye-mountable device. For instance, an example method for fabricating an eye-mountable device may involve: (i) forming a first polymer layer, wherein the first polymer layer defines a posterior side of the eye-mountable device; (ii) positioning a sensor apparatus on the first polymer layer; and (iii) forming a second polymer layer over the first polymer layer and the sensor apparatus, such that the sensor apparatus is fully enclosed by the first polymer layer and the second polymer layer, wherein the second polymer layer defines an anterior side of the eye-mountable device and is configured to allow an analyte to diffuse therethrough. In this example, the at least one sensor may be oriented relative to the second polymer layer to receive the analyte via diffusion through the second polymer layer.

E. Forming Interlocking Features in the First and Second Polymer Layers

As mentioned above, in an exemplary embodiment the disclosed method involves partially curing the first polymer layer. Additionally or alternatively, the disclosed method may involve the formation of interlocking features on the first polymer layer and the second polymer layer. Further, the sensor apparatus may also include interlocking features. These interlocking features may beneficially influence the placement of the sensor apparatus in a precise location. Further, these interlocking features may also help the sensor apparatus to remain in a fixed location during subsequent formation steps.

Figure 3:
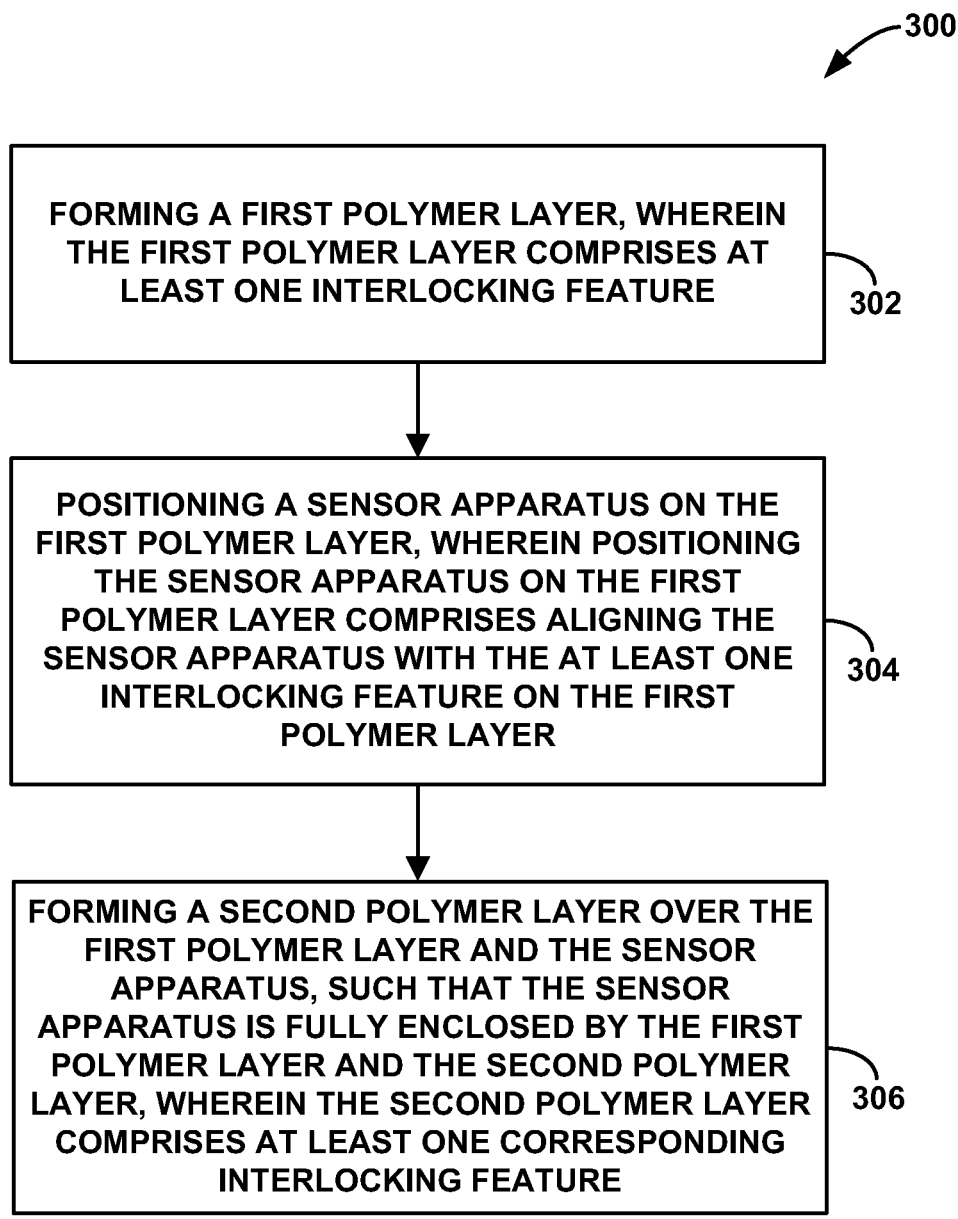
FIG. 3 is a flow chart illustrating a method according to an example embodiment.

FIG. 3 is a flow chart illustrating a method according to an example embodiment in which the polymer layers have interlocking features. In particular, FIG. 3 shows a method 300 for fabricating an eye-mountable device. Furthermore, method 300 is similar in many respects to method 100, and thus is not described in as great of detail. It should be explicitly noted, however, that any possibilities and permutations described above with respect to method 100 may apply equally to method 300.

More specifically, example method 300 involves forming a first polymer layer, wherein the first polymer layer comprises at least one interlocking feature, as shown by block 302. The method may then involve positioning a sensor apparatus on the first polymer layer, wherein positioning the sensor apparatus on the first polymer layer comprises aligning the sensor apparatus with the at least one interlocking feature on the first polymer layer, as shown by block 304. Further, the method may then involve forming a second polymer layer over the first polymer layer and the sensor apparatus, such that the sensor apparatus is fully enclosed by the first polymer layer and the second polymer layer, wherein the second polymer layer comprises at least one corresponding interlocking feature, as shown by block 306.

Method 300 is described in further detail with reference to FIG. 4, which is an exploded view of a cross-section of an eye-mountable device 400. As mentioned above, at block 302, the fabrication device may form a first polymer layer 402. This first polymer layer 402 may include at least one interlocking feature, such as interlocking feature 404. Interlocking feature 404 is a protrusion in the first polymer layer 402. Further, this interlocking feature 404 has a diameter that corresponds to an inner diameter 412 of sensor apparatus 406.

At block 304, the fabrication device may position sensor apparatus 406 on the first polymer layer 402. Sensor apparatus 406 may include a ring-shaped support with at least one sensor, such as sensor 407. The interlocking feature 404 may be used by the fabrication device to aid with the positioning of the sensor apparatus. In particular, the fabrication device may position the sensor apparatus 406 on the first polymer layer 402 by aligning the sensor apparatus 406 with the interlocking feature 404. In the example of FIG. 4, since the interlocking feature 404 has a diameter that corresponds to the inner diameter of the sensor apparatus, the sensor apparatus 406 will fit over the interlocking feature 404. Further, the interlocking feature 404 may then allow the sensor apparatus 406 to remain fixed to the first polymer layer 402 during formation of the second polymer layer. This first polymer layer 402 may also be partially cured so that the first polymer layer 402 has a tackiness that facilitates adhesion of the sensor apparatus 406 thereto. In another example, an adhesive may also be placed on the first polymer layer 402 and/or the sensor apparatus 406 that facilitates adhesion of the sensor apparatus 406 to the first polymer layer 402.

Figure 4:
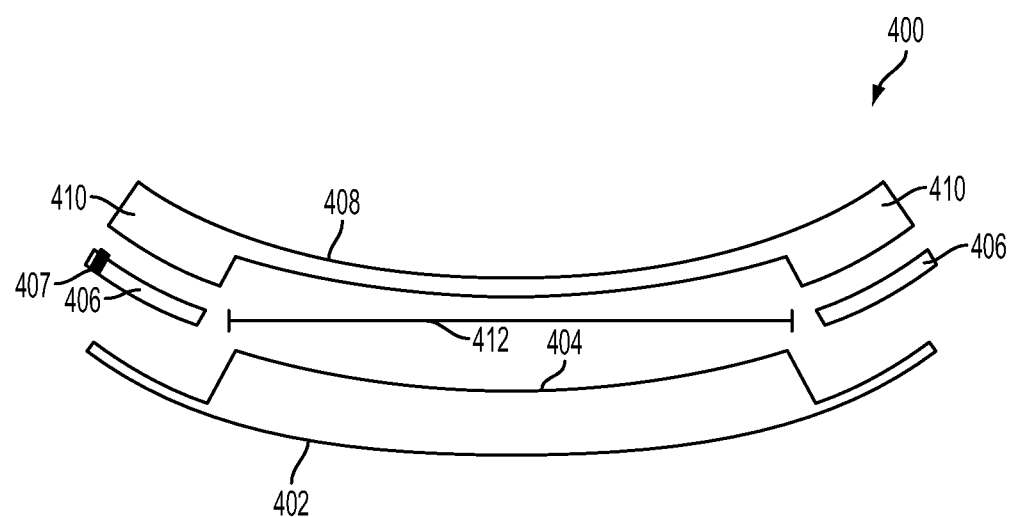
FIG. 4 illustrates an exploded view of an example eye-mountable device, according to an example embodiment.

In this example of FIG. 4, the at least one sensor 407 of the sensor apparatus 406 may be oriented relative to the first polymer layer 402 to receive the analyte via diffusion through the first polymer layer 402. Although the first polymer layer 402 as formed may have a maximum thickness over 50 micrometers where the interlocking feature 404 is located, the thickness of the polymer layer on which the sensor 407 is located may be less than 50 micrometers. As such, where the sensor 407 is positioned, the polymer layer 402 may allow for sufficient diffusion of a given analyte.

Next, as mentioned above, at block 306, the fabrication device may form a second polymer layer over the first polymer layer and the sensor apparatus, such that the sensor apparatus is fully enclosed by the first polymer layer and the second polymer layer. The second polymer layer may include at least one corresponding interlocking feature. In particular, fabrication device may form a second polymer layer 408 over the first polymer layer 402 and the sensor apparatus 406, such that the sensor apparatus 406 is fully enclosed by the first polymer layer 402 and the second polymer layer 408. In addition, the second polymer 408 layer may include an interlocking feature 410 that corresponds to interlocking feature 404. Since in the example of FIG. 4 interlocking feature 404 is a protrusion, interlocking feature 410 is a corresponding indentation having dimensions corresponding to the protrusion.

Although FIG. 4 depicts a single interlocking feature in the form of a protrusion, other numbers and/or types of interlocking features are possible as well. In general, the interlocking feature may be any feature that helps align the sensor apparatus. For instance, the first polymer layer 402 may comprise a plurality of interlocking features. For example, the first polymer layer may comprise four rods protruding from the polymer layer at 0 degrees, 90 degrees, 180 degrees, and 240 degrees, respectively. In such an example, the sensor apparatus may be configured to be positioned between the four rods. These four rods may form a circle having a given diameter, and the outer diameter of the sensor apparatus may be slightly smaller than the diameter of the circle formed by the rods. Thus, in such an example, the sensor apparatus may be positioned between the four rods and the four rods may hold the sensor apparatus in place during the formation of the second layer.

In yet another example where the interlocking features are four rods, the sensor apparatus may comprise four holes in the sensor apparatus that are configured to receive the four rods as the sensor apparatus is positioned on the first polymer layer. In such an example, these holes in the sensor apparatus may have a diameter that corresponds to the diameter of the rods. In another example, the first polymer layer may include indentations, while the sensor apparatus includes protrusions that are configured to fit in those indentations. Other types of interlocking features are possible as well.

F. Forming the First Polymer Layer and the Second Polymer Layer at the Same Time The example methods described above involve a method of fabricating an eye-mountable device that involves first forming a first polymer layer and subsequently forming a second polymer layer. In another example, the first polymer layer defining an anterior side of the eye-mountable device and the second polymer layer defining a posterior side of the eye-mountable device may be formed or substantially formed around the sensor apparatus at the same time. Further, in such an example, positioning the sensor apparatus on the first layer would take place at the same time as the formation of the first polymer layer and the second polymer layer.

For instance, in accordance with an example embodiment, the fabrication device may be configured to position a sensor apparatus within a molding cavity or cavities, and the fabrication device may then form the first polymer layer and the second polymer layer around the sensor apparatus. In such an example, the fabrication device may be configured to inject mold into the molding cavity, and the injected mold may encapsulate the sensor apparatus. In this example, the fabrication device may include a molding cavity or cavities that have at least one opening configured to allow the fabrication device to hold the sensor apparatus in place as the first and second polymer layers are formed around the sensor apparatus. The molding cavity or cavities may be filled with the polymer material, and this introduction of the polymer material may form the polymer layers around the sensor apparatus.

Figure 5A:
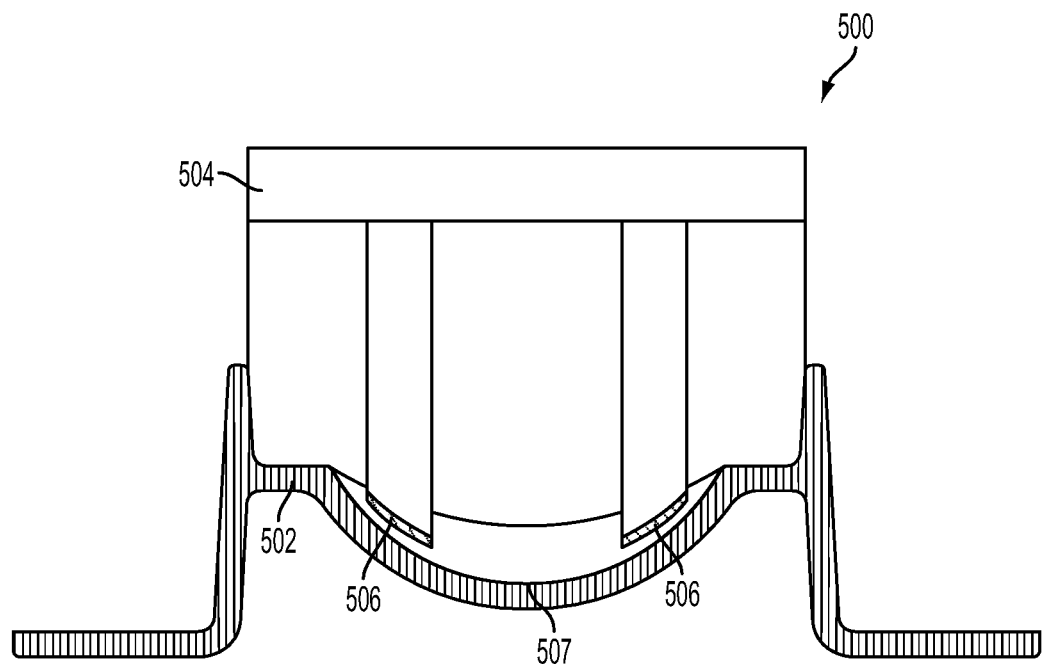
FIG. 5a is an illustration of positioning of a sensor apparatus prior to formation of a first polymer layer and a second polymer layer around the sensor apparatus, according to an example embodiment.

FIGS. 5a-5e illustrate an example of fabrication of an eye-mountable device where the first polymer layer and the second polymer layer are substantially formed at the same time. In particular, as shown in FIG. 5a, fabrication device 500 may include a molding cavity 502 and a positioning apparatus 504. In this example, positioning apparatus 504 also acts as a top molding cavity. Further, the molding cavity 502 defines the anterior side of the eye-mountable device, whereas the positioning apparatus 504 defines the posterior side of the eye-mountable device.

The positioning apparatus 504 may position a sensor apparatus 506 within the molding cavity 502 so that the first polymer layer and the second polymer layer may be formed around the sensor apparatus. In an example, the positioning apparatus 504 holds the sensor apparatus 506 via suction, so that the sensor apparatus 506 is held at a given distance from the bottom 507 of the molding cavity 502. In addition to or as an alternative to suction, the positioning apparatus could grasp the sensor apparatus in various other ways, such as any suitable mechanical gripping.

Figure 5B:
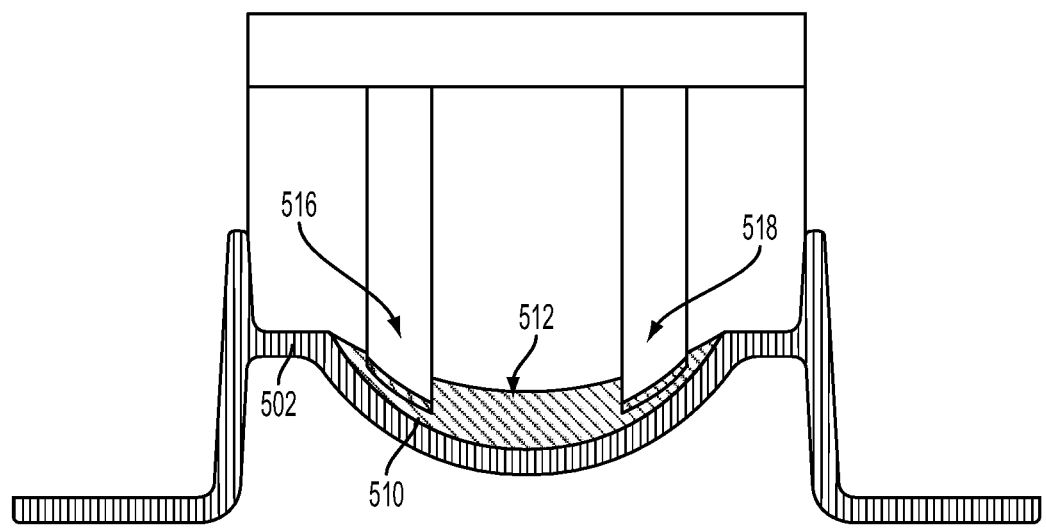
FIG. 5b is an illustration of formation of a first polymer layer and a second polymer layer, according to an example embodiment.

As shown in FIG. 5b, the fabrication device 500 may form the first polymer layer 510 and second polymer layer 512 at the same time. These layers may, for example, be formed via cast molding or injection molding. After these layers are formed, the positioning apparatus 504 may release the sensor apparatus 506, and the fabrication device 500 may then remove the positioning apparatus 504 from the molding cavity 502.

As a result of the formation of these layers, the eye-mountable device 514 is substantially formed. However, since the positioning apparatus 504 was holding the sensor apparatus 506 firmly in place as the first polymer layer 510 and second polymer layer 512 were formed, there will be voids in the eye-mountable device 514 where polymer has yet to be introduced. For instance, the positioning apparatus 504 may include features that hold the sensor apparatus in place, and these features will prevent the fabrication device from filling in polymer layers where the features are within the molding cavities 502, 504.

Figure 5C:
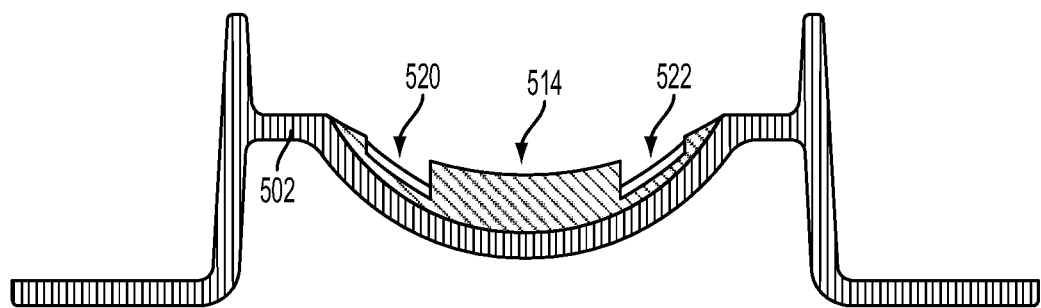
FIGS. 5c-d are illustrations of the eye-mountable device formed in FIG. 5b, after the positioning apparatus is removed, according to an example embodiment.
Figure 5D:
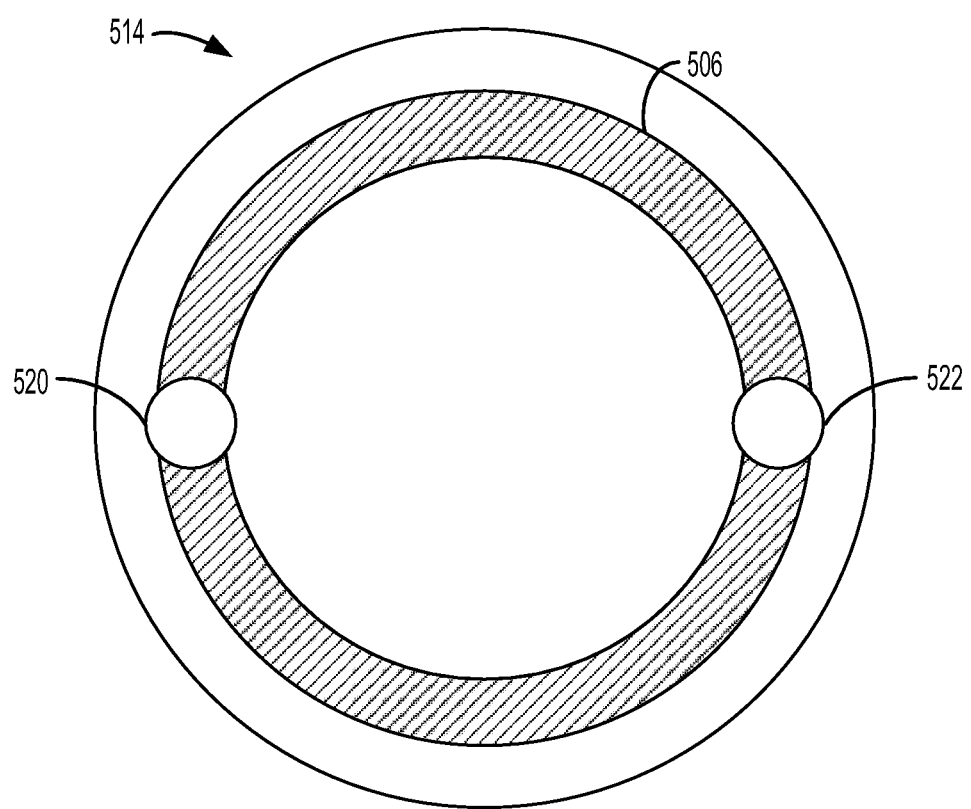

As an example, with reference to FIG. 5b, positioning apparatus 504 may include arms 516, 518, that act to suction the sensor apparatus 506 in place during formation of the polymer layers 510, 512. When these arms 516, 518 are removed after formation of layers 510 and 512, there will be holes in the eye-mountable device 514 where the arms were previously positioned. FIG. 5c illustrates a cross-sectional view of the eye-mountable device 514 after the arms 516, 518 are removed. Further, FIG. 5d illustrates a top view of the eye-mountable device after the arms 516, 518 have been removed. As is clear from FIGS. 5c-d, the eye-mountable device 514 includes holes 520, 522 where polymer is lacking.

Figure 5E:
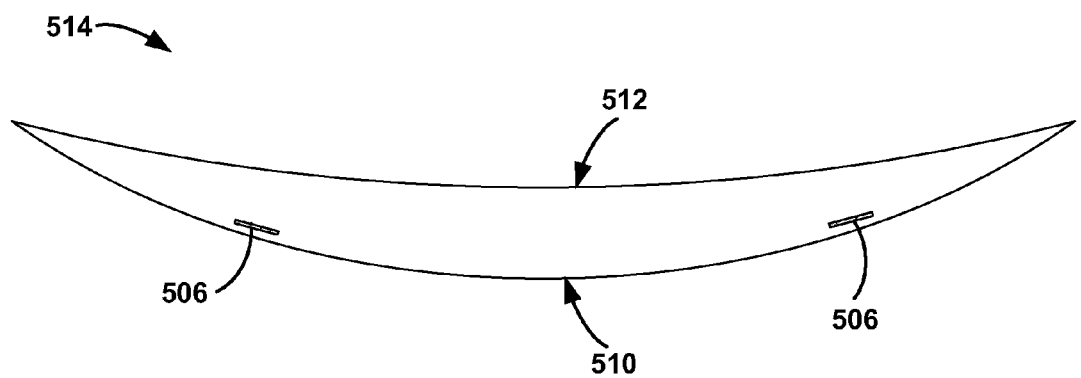
FIG. 5e is an illustration of an example eye-mountable device, according to an example embodiment.

The fabrication device 500 may then introduce a second shot of polymer material in order to fill in holes 520 and 522 left by the positioning apparatus arms 516, 518. For instance, the fabrication device 500 may introduce a second shot of polymer to fill in holes 520, 522. As a result of filling in these holes 520, 522, the sensor apparatus 506 will be fully enclosed by polymer (as shown in FIG. 5e). It should be understood that, while the void cause by the positioning apparatus 504 are depicted as holes in FIGS. 5c-5d due to the arms being shaped as rods, the voids left by the positioning apparatus 504 may take various forms. For instance, the voids may appear as slots due to arms of a different shape.

G. Sensor Oriented Relative to the Posterior Side of the Eye-Mountable Device

In the examples described above, the eye-mountable devices are fabricated such that the at least one sensor is oriented relative to the first polymer layer to receive the analyte via diffusion through the first polymer layer, where the first polymer layer defines an anterior side of the eye-mountable device. However, in other examples, an eye-mountable device may be fabricated such that the at least one sensor is oriented relative to a polymer layer to receive the analyte via diffusion through the polymer layer, where the polymer layer defines a posterior side of the eye-mountable device.

Figure 6:
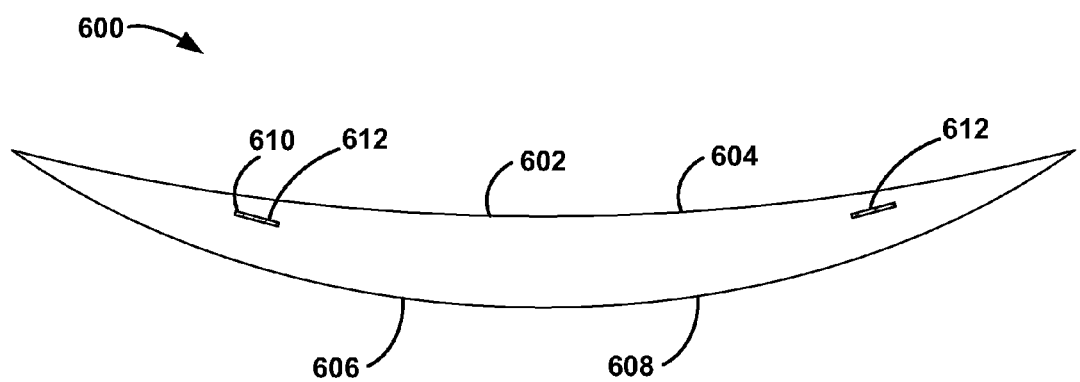
FIG. 6 is an illustration of an example eye-mountable device, according to an example embodiment.

FIG. 6 illustrates an example eye-mountable device in which the sensor apparatus is oriented relative to a polymer layer that defines the posterior side of the device. In particular, eye-mountable device 600 has a first polymer layer 602 that defines a posterior side 604 of the device, and a second polymer layer 606 that defines an anterior side 608 of the device 600. Sensor apparatus 610 is positioned within the device such that at least one sensor 610 of the sensor apparatus 612 is oriented relative to the first polymer layer 602 to receive the analyte via diffusion through the first polymer layer 602. It should be understood that a device such as eye-mountable device 600 may be formed in accordance with the methods and devices described above, where the methods and device above are adjusted to form the thin polymer layer (e.g., a polymer layer of less than 50 micrometers) at the posterior side of the eye-mountable device.

As mentioned above, it may be desirable to manufacture eye-mountable devices on a large scale. Further, when manufacturing eye-mountable devices on a large scale, it may be desirable to fabricate a large number of eye-mountable devices that each meet well-defined specifications (e.g., specifications within given manufacturing tolerances). For example, it may be desirable that each fabricated device has an anterior layer covering the sensor apparatus, where the anterior layer has a well-defined thickness. Further, it may be desirable that each eye-mountable device has a sensor apparatus located at a precise location within the eye-mountable device. The disclosed exemplary methods beneficially allow for repeatable results, in which the sensor apparatus is located in a precise location and there is a polymer layer over the sensor apparatus that has a well-defined thickness.

III. EXAMPLE SYSTEMS AND DEVICES

As mentioned above, an eye-mountable device may be fabricated using the example methods described above. Further, this eye-mountable device may be configured to monitor health-related information based on at least one analyte detected from an eye of a user wearing the eye-mountable device. An example eye-mountable device configured to monitor health-related information based on at least one analyte detected from an eye of a user is described in greater detail below with reference to FIGS. 7 and 8a-d.

A sensor apparatus in accordance with an exemplary embodiment may include a sensor, control electronics and an antenna all situated on a substrate. The control electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that diffuses through the anterior side of the eye-mountable device. For example, the sensor apparatus can be suspended in the lens material and situated such that the sensor is less than 10 micrometers from the anterior edge of the eye-mountable device. In another example, the sensor can be arranged on the substrate to face inward, toward the corneal surface, so as to generate clinically relevant readings from near the surface of the cornea and/or from tear fluid interposed between the contact lens and the corneal surface. The sensor can generate an output signal indicative of a concentration of an analyte that diffuses through the lens material to the embedded sensor.

Figure 7:
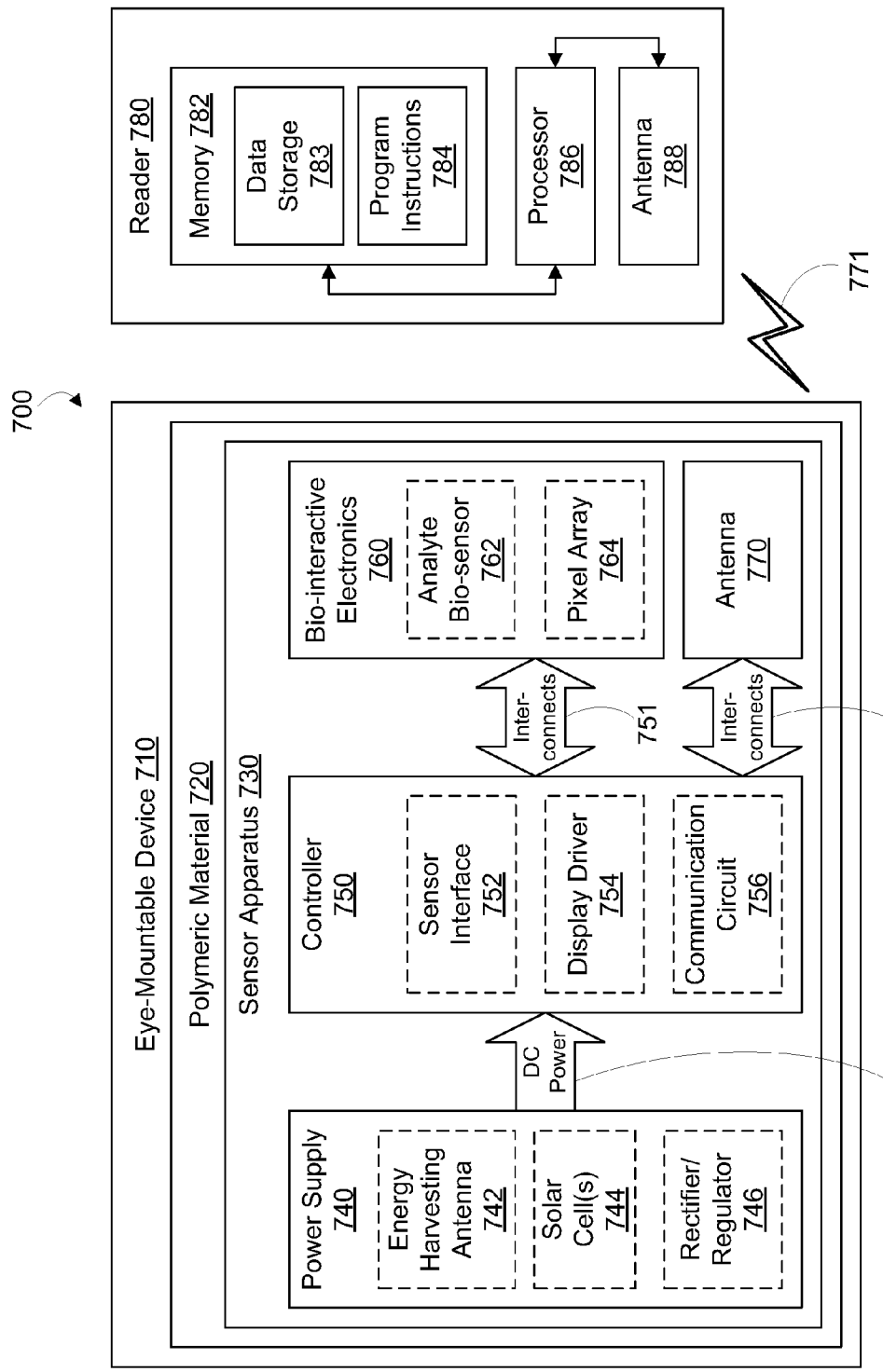
FIG. 7 is a block diagram of a system with an eye-mountable device in wireless communication with an external reader, according to an example embodiment.

FIG. 7 is a block diagram of a system 700 with an eye-mountable device 710 in wireless communication with an external reader 780. The exposed regions of the eye-mountable device 710 are made of a polymeric material 720 formed to be contact-mounted to a corneal surface of an eye. In accordance with the exemplary methods, polymeric material 720 may comprise a first polymer layer and a second polymer layer.

The sensor apparatus may comprise a substrate, such as substrate 730 that is embedded in the polymeric material 720 to provide a mounting surface for a power supply 740, a controller 750, bio-interactive electronics 760, and a communication antenna 770. The bio-interactive electronics 760 are operated by the controller 750. The power supply 740 supplies operating voltages to the controller 750 and/or the bio-interactive electronics 760. The antenna 770 is operated by the controller 750 to communicate information to and/or from the eye-mountable device 710. The antenna 770, the controller 750, the power supply 740, and the bio-interactive electronics 760 can all be situated on the embedded substrate 730. Because the eye-mountable device 710 includes electronics and is configured to be contact-mounted to an eye, it may also be referred to as an ophthalmic electronics platform.

To facilitate contact-mounting, the polymeric material 720 can have a concave surface configured to adhere ("mount") to a moistened corneal surface (e.g., by capillary forces with a tear film coating the corneal surface). Additionally or alternatively, the eye-mountable device 710 can be adhered by a vacuum force between the corneal surface and the polymeric material due to the concave curvature. While mounted with the concave surface against the eye, the anterior or outward-facing surface of the polymeric material 720 can have a convex curvature that is formed to not interfere with eye-lid motion while the eye-mountable device 710 is mounted to the eye. For example, the polymeric material 720 can be a substantially transparent curved polymeric disk shaped similarly to a contact lens.

The polymeric material 720 can include one or more biocompatible materials, such as those employed for use in contact lenses or other ophthalmic applications involving direct contact with the corneal surface. The polymeric material 720 can optionally be formed in part from such biocompatible materials or can include an outer coating with such biocompatible materials. The polymeric material 720 can include materials configured to moisturize the corneal surface, such as hydrogels and the like. In some instances, the polymeric material 720 can be a deformable ("non-rigid") material to enhance wearer comfort. In some instances, the polymeric material 720 can be shaped to provide a predetermined, vision-correcting optical power, such as can be provided by a contact lens.

The substrate 730 includes one or more surfaces suitable for mounting the bio-interactive electronics 760, the controller 750, the power supply 740, and the antenna 770. The substrate 730 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 730 to form circuitry, electrodes, etc. For example, the antenna 770 can be formed by depositing a pattern of gold or another conductive material on the substrate 730. Similarly, interconnects 751, 757 between the controller 750 and the bio-interactive electronics 760, and between the controller 750 and the antenna 770, respectively, can be formed by depositing suitable patterns of conductive materials on the substrate 730. A combination of resists, masks, and deposition techniques can be employed to pattern materials on the substrate 730.

The substrate 730 can be a relatively rigid material, such as polyethylene terephthalate ("PET") or another material sufficient to structurally support the circuitry and/or electronics within the polymeric material 720. The eye-mountable device 710 can alternatively be arranged with a group of unconnected substrates rather than a single substrate. For example, the controller 750 and a bio-sensor or other bio-interactive electronic component can be mounted to one substrate, while the antenna 770 is mounted to another substrate and the two can be electrically connected via the interconnects 757.

In some embodiments, the bio-interactive electronics 760 (and the substrate 730) can be positioned away from the center of the eye-mountable device 710 and thereby avoid interference with light transmission to the eye through the center of the eye-mountable device 710. For example, where the eye-mountable device 710 is shaped as a concave-curved disk, the substrate 730 can be embedded around the periphery (e.g., near the outer circumference) of the disk. In some embodiments, the bio-interactive electronics 760 (and the substrate 730) can be positioned in the center region of the eye-mountable device 710. The bio-interactive electronics 760 and/or substrate 730 can be substantially transparent to incoming visible light to mitigate interference with light transmission to the eye. Moreover, in some embodiments, the bio-interactive electronics 760 can include a pixel array 764 that emits and/or transmits light to be perceived by the eye according to display driver instructions. Thus, the bio-interactive electronics 760 can optionally be positioned in the center of the eye-mountable device so as to generate perceivable visual cues to a wearer of the eye-mountable device 710, such as by displaying information via the pixel array 764.

The substrate 730 can be shaped as a flattened ring with a radial width dimension sufficient to provide a mounting platform for the embedded electronics components. The substrate 730 can have a thickness sufficiently small to allow the substrate 730 to be embedded in the polymeric material 720 without influencing the profile of the eye-mountable device 710. The substrate 730 can have a thickness sufficiently large to provide structural stability suitable for supporting the electronics mounted thereon. For example, the substrate 730 can be shaped as a ring with a diameter of about 10 millimeters, a radial width of about 1 millimeter (e.g., an outer radius 1 millimeter larger than an inner radius), and a thickness of about 50 micrometers. The substrate 730 can optionally be aligned with the curvature of the anterior side of the eye-mountable device.

The power supply 740 is configured to harvest ambient energy to power the controller 750 and bio-interactive electronics 760. For example, a radio-frequency energy-harvesting antenna 742 can capture energy from incident radio radiation. Additionally or alternatively, solar cell(s) 744 ("photovoltaic cells") can capture energy from incoming ultraviolet, visible, and/or infrared radiation. Furthermore, an inertial power scavenging system can be included to capture energy from ambient vibrations. The energy harvesting antenna 742 can optionally be a dual-purpose antenna that is also used to communicate information to the external reader 780. That is, the functions of the communication antenna 770 and the energy harvesting antenna 742 can be accomplished with the same physical antenna.

A rectifier/regulator 746 can be used to condition the captured energy to a stable DC supply voltage 741 that is supplied to the controller 750. For example, the energy harvesting antenna 742 can receive incident radio frequency radiation. Varying electrical signals on the leads of the antenna 742 are output to the rectifier/regulator 746. The rectifier/regulator 746 rectifies the varying electrical signals to a DC voltage and regulates the rectified DC voltage to a level suitable for operating the controller 750. Additionally or alternatively, output voltage from the solar cell(s) 744 can be regulated to a level suitable for operating the controller 750. The rectifier/regulator 746 can include one or more energy storage devices arranged to mitigate high frequency variations in the ambient energy gathering antenna 742 and/or solar cell(s) 744. For example, an energy storage device (e.g., capacitor, inductor, etc.) can be connected to the output of the rectifier 746 so as to function as a low-pass filter.

The controller 750 is turned on when the DC supply voltage 741 is provided to the controller 750, and the logic in the controller 750 operates the bio-interactive electronics 760 and the antenna 770. The controller 750 can include logic circuitry configured to operate the bio-interactive electronics 760 so as to interact with a biological environment of the eye-mountable device 710. The interaction could involve the use of one or more components, such as an analyte bio-sensor 762, in bio-interactive electronics 760 to obtain input from the biological environment. Alternatively or additionally, the interaction could involve the use of one or more components, such as pixel array 764, to provide an output to the biological environment.

In one example, a sensor interface module 752 can be included for operating the analyte bio-sensor 762. The analyte bio-sensor 762 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 752 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOD") can be situated around the working electrode to catalyze glucose into hydrogen peroxide ($H_2O_2$). The hydrogen peroxide can then be oxidized at the working electrode, which releases electrons to the working electrode, which generates a current.

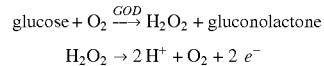

$$H_2O_2 \rightarrow 2H^+ + O_2 + 2\,e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current thus provides an indication of the analyte concentration.

The controller 750 can optionally include a display driver module 754 for operating a pixel array 764. The pixel array 764 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 754. Such a pixel array 764 can also optionally include more than one color of pixels (e.g., red, green, and blue pixels) to render visual content in color. The display driver module 754 can include, for example, one or more data lines providing programming information to the separately programmed pixels in the pixel array 764 and one or more addressing lines for setting groups of pixels to receive such programming information. Such a pixel array 764 situated on the eye can also include one or more lenses to direct light from the pixel array to a focal plane perceivable by the eye.

The controller 750 can also include a communication circuit 756 for sending and/or receiving information via the antenna 770. The communication circuit 756 can optionally include one or more oscillators, mixers, frequency injectors, etc. to modulate and/or demodulate information on a carrier frequency to be transmitted and/or received by the antenna 770. In some examples, the eye-mountable device 710 is configured to indicate an output from a bio-sensor by modulating an impedance of the antenna 770 in a manner that is perceivably by the external reader 780. For example, the communication circuit 756 can cause variations in the amplitude, phase, and/or frequency of backscatter radiation from the antenna 770, and such variations can be detected by the reader 780.

The controller 750 is connected to the bio-interactive electronics 760 via interconnects 751. For example, where the controller 750 includes logic elements implemented in an integrated circuit to form the sensor interface module 752 and/or display driver module 754, a patterned conductive material (e.g., gold, platinum, palladium, titanium, copper, aluminum, silver, metals, combinations of these, etc.) can connect a terminal on the chip to the bio-interactive electronics 760. Similarly, the controller 750 is connected to the antenna 770 via interconnects 757.

It is noted that the block diagram shown in FIG. 7 is described in connection with functional modules for convenience in description. However, embodiments of the eye-mountable device 710 can be arranged with one or more of the functional modules ("sub-systems") implemented in a single chip, integrated circuit, and/or physical feature. For example, while the rectifier/regulator 746 is illustrated in the power supply block 740, the rectifier/regulator 746 can be implemented in a chip that also includes the logic elements of the controller 750 and/or other features of the embedded electronics in the eye-mountable device 710. Thus, the DC supply voltage 741 that is provided to the controller 750 from the power supply 740 can be a supply voltage that is provided on a chip by rectifier and/or regulator components the same chip. That is, the functional blocks in FIG. 7 shown as the power supply block 740 and controller block 750 need not be implemented as separated modules. Moreover, one or more of the functional modules described in FIG. 7 can be implemented by separately packaged chips electrically connected to one another.

Additionally or alternatively, the energy harvesting antenna 742 and the communication antenna 770 can be implemented with the same physical antenna. For example, a loop antenna can both harvests incident radiation for power generation and communicate information via backscatter radiation.

The external reader 780 includes an antenna 788 (or group of more than one antennae) to send and receive wireless signals 771 to and from the eye-mountable device 710. The external reader 780 also includes a computing system with a processor 786 in communication with a memory storage 782. The memory 782 is a non-transitory computer-readable medium that can include, without limitation, magnetic disks, optical disks, organic memory, and/or any other volatile (e.g. RAM) or non-volatile (e.g. ROM) storage system readable by the processor 786. The memory 782 can include a data storage 783 to store indications of data structures, such as sensor readings (e.g., from the analyte bio-sensor 762), program settings (e.g., to adjust behavior of the eye-mountable device and/or external reader 780), etc. The memory can also include program instructions 784 for execution by the processor 786 to cause the external reader to perform processes specified by the instructions 784. For example, the program instructions 784 can cause external reader 780 to provide a user interface that allows for retrieving information communicated from the eye-mountable device 710 (e.g., sensor outputs from the analyte bio-sensor 762). The external reader 780 can also include one or more hardware components for operating the antenna 788 to send and receive the wireless signals 771 to and from the eye-mountable device 710. For example, oscillators, frequency injectors, encoders, decoders, amplifiers, filters, etc. can drive the antenna 788 according to instructions from the processor 786.

The external reader 780 can be a smart phone, digital assistant, or other portable computing device with wireless connectivity sufficient to provide the wireless communication link 771. The external reader 780 can also be implemented as an antenna module that can be plugged in to a portable computing device, such as in an example where the communication link 771 operates at carrier frequencies not commonly employed in portable computing devices. In some instances, the external reader 780 is a special-purpose device configured to be worn relatively near a wearer's eye to allow the wireless communication link 771 to operate with a low power budget. For example, the external reader 780 can be integrated in a piece of jewelry such as a necklace, earing, etc. or integrated in an article of clothing worn near the head, such as a hat, headband, etc.

In an example where the eye-mountable device 710 includes an analyte bio-sensor 762, the system 700 can be operated to monitor the analyte concentration in tear film on the surface of the eye. Thus, the eye-mountable device 710 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 700 configured as a tear film analyte monitor, the external reader 780 can emit radio frequency radiation 771 that is harvested to power the eye-mountable device 710 via the power supply 740. Radio frequency electrical signals captured by the energy harvesting antenna 742 (and/or the communication antenna 770) are rectified and/or regulated in the rectifier/regulator 746 and a regulated DC supply voltage 747 is provided to the controller 750. The radio frequency radiation 771 thus turns on the electronic components within the eye-mountable device 710. Once turned on, the controller 750 operates the analyte bio-sensor 762 to measure an analyte concentration level. For example, the sensor interface module 752 can apply a voltage between a working electrode and a reference electrode in the analyte bio-sensor 762 sufficient to cause the analyte to undergo an electrochemical reaction at the working electrode. The current through the working electrode can be measured to provide the sensor output indicative of the analyte concentration. The controller 750 can operate the antenna 770 to communicate the sensor results back to the external reader 780 (e.g., via the communication circuit 756). The sensor result can be communicated by, for example, modulating an impedance of the communication antenna 770 such that the modulation in impedance is detected by the external reader 780. The modulation in antenna impedance can be detected by, for example, backscatter radiation from the antenna 770.

In some embodiments, the system 700 can operate to non-continuously ("intermittently") supply energy to the eye-mountable device 710 to power the on-board controller 750 and electronics 760. For example, radio frequency radiation 771 can be supplied to power the eye-mountable device 710 long enough to carry out a tear film analyte concentration measurement and communicate the results.

For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 771 can be considered an interrogation signal from the external reader 780 to the eye-mountable device 710 to request a measurement. By periodically interrogating the eye-mountable device 710 (e.g., by supplying radio frequency radiation 771 to temporarily turn the device on) and storing the sensor results (e.g., via the data storage 783), the external reader 780 can accumulate a set of analyte concentration measurements over time without continuously powering the eye-mountable device 110.

Figure 8A:
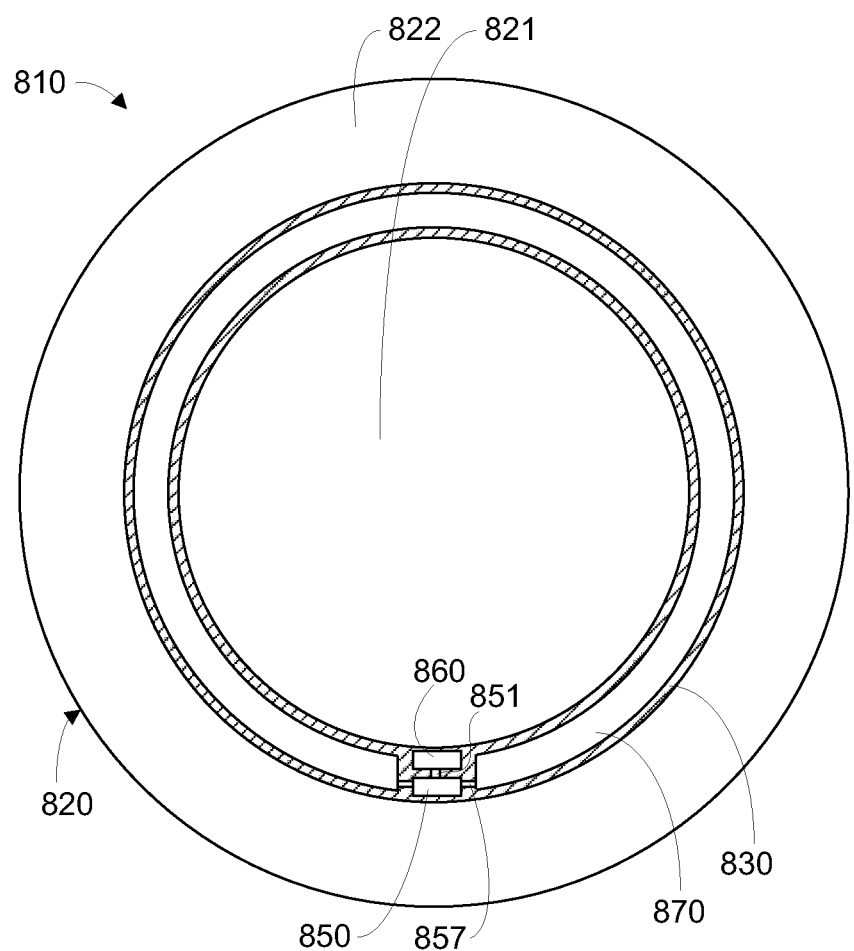
FIG. 8a is a top view of an example eye-mountable device, according to an example embodiment.
Figure 8B:
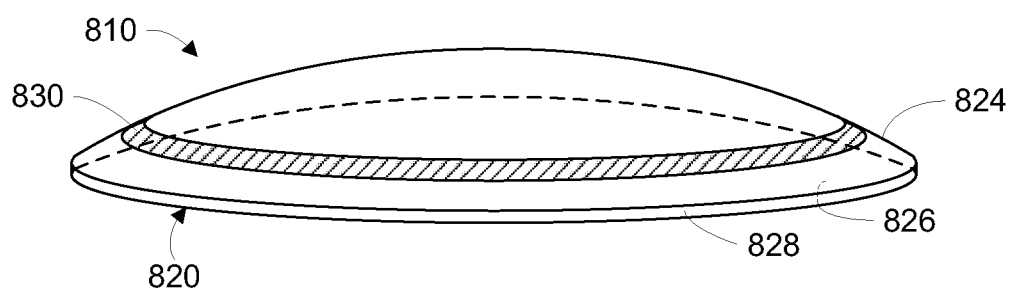

FIG. 8a is a top view of an example eye-mountable electronic device 810. FIG. 8b is an aspect view of the example eye-mountable electronic device shown in FIG. 8a. It is noted that relative dimensions in FIGS. 8a and 8b are not necessarily to scale, but have been rendered for purposes of explanation only in describing the arrangement of the example eye-mountable electronic device 810. The eye-mountable device 810 is formed of a polymeric material 820 shaped as a curved disk. The polymeric material 820 can be a substantially transparent material to allow incident light to be transmitted to the eye while the eye-mountable device 810 is mounted to the eye. The polymeric material 820 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 820 can be formed with one side having a concave surface 826 suitable to fit over a corneal surface of an eye. The opposing side of the disk can have a convex surface 824 that does not interfere with eyelid motion while the eye-mountable device 810 is mounted to the eye. A circular outer side edge 828 connects the concave surface 824 and convex surface 826.

The eye-mountable device 810 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 810 can be selected according to the size and/or shape of the corneal surface of the wearer's eye.

While the eye-mountable device 810 is mounted in an eye, the convex surface 824 (i.e., the anterior surface) faces outward to the ambient environment while the concave surface 826 (i.e., the posterior surface) faces inward, toward the corneal surface. The convex surface 824 can therefore be considered an outer, top surface of the eye-mountable device 810 whereas the concave surface 826 can be considered an inner, bottom surface. The "top" view shown in FIG. 8a is facing the convex surface 824.

A substrate 830 is embedded in the polymeric material 820. The substrate 830 can be embedded to be situated along the outer periphery 822 of the polymeric material 820, away from the center region 821. The substrate 830 does not interfere with vision because it is too close to the eye to be in focus and is positioned away from the center region 821 where incident light is transmitted to the eye-sensing portions of the eye. Moreover, the substrate 830 can be formed of a transparent material to further mitigate any effects on visual perception.

The substrate 830 can be shaped as a flat, circular ring (e.g., a disk with a central hole). The flat surface of the substrate 830 (e.g., along the radial width) is a platform for mounting electronics such as chips (e.g., via flip-chip mounting) and for patterning conductive materials (e.g., via deposition techniques) to form electrodes, antenna(e), and/or connections. The substrate 830 and the polymeric material 820 can be approximately cylindrically symmetric about a common central axis. The substrate 830 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 830 can be implemented in a variety of different form factors.

A loop antenna 870, controller 850, and bio-interactive electronics 860 are disposed on the embedded substrate 830. The controller 850 can be a chip including logic elements configured to operate the bio-interactive electronics 860 and the loop antenna 870. The controller 850 is electrically connected to the loop antenna 870 by interconnects 857 also situated on the substrate 830. Similarly, the controller 850 is electrically connected to the bio-interactive electronics 860 by an interconnect 851. The interconnects 851, 857, the loop antenna 870, and any conductive electrodes (e.g., for an electrochemical analyte bio-sensor, etc.) can be formed from conductive materials patterned on the substrate 830 by a process for precisely patterning such materials, such as deposition or lithography. The conductive materials patterned on the substrate 830 can be, for example, gold, platinum, palladium, titanium, carbon, aluminum, copper, silver, silver-chloride, conductors formed from noble materials, metals, combinations of these, etc.

With reference to FIG. 8a, which is a view facing the convex surface 824 of the eye-mountable device 810, the bio-interactive electronics module 860 is mounted to a side of the substrate 830 facing the convex surface 824. Where the bio-interactive electronics module 860 includes an analyte bio-sensor, for example, mounting such a bio-sensor on the substrate 830 to be close to the convex surface 824 allows the bio-sensor to sense analyte concentrations in tear film near the anterior surface of the device. However, the electronics, electrodes, etc. situated on the substrate 830 can be mounted to either the "inward" facing side (e.g., situated closest to the concave surface 826 when the thin polymer layer is located on the posterior side of the eye-mountable device) or the "outward" facing side (e.g., situated closest to the convex surface 824 when the thin polymer layer is located on the anterior side of the eye-mountable device). Moreover, in some embodiments, some electronic components can be mounted on one side of the substrate 830, while other electronic components are mounted to the opposing side, and connections between the two can be made through conductive materials passing through the substrate 830.

The loop antenna 870 is a layer of conductive material patterned along the flat surface of the substrate to form a flat conductive ring. In some instances, the loop antenna 870 can be formed without making a complete loop. For instance, the loop antenna can have a cutout to allow room for the controller 850 and bio-interactive electronics 860, as illustrated in FIG. 8a. However, the loop antenna 870 can also be arranged as a continuous strip of conductive material that wraps entirely around the flat surface of the substrate 830 one or more times. For example, a strip of conductive material with multiple windings can be patterned on the side of the substrate 830 opposite the controller 850 and bio-interactive electronics 860. Interconnects between the ends of such a wound antenna (e.g., the antenna leads) can be passed through the substrate 830 to the controller 850.

FIG. 8c is a side cross-section view of the example eye-mountable electronic device 810 while mounted to a corneal surface 22 of an eye 10. FIG. 8d is a close-in side cross-section view enhanced to show the tear film layers 40, 42 surrounding the exposed surfaces 824, 826 of the example eye-mountable device 810. It is noted that relative dimensions in FIGS. 8c and 8d are not necessarily to scale, but have been rendered for purposes of explanation only in describing the arrangement of the example eye-mountable electronic device 810. For example, the total thickness of the eye-mountable device can be about 200 micrometers, while the thickness of the tear film layers 40, 42 can each be about 10 micrometers, although this ratio is may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 810 is mounted in the eye 10, the tear film coats both the convex and concave surfaces 824, 826 with an inner layer 40 (along the concave surface 826) and an outer layer 42 (along the convex layer 824). The tear film layers 40, 42 can be about 10 micrometers in thickness and together account for about 10 microliters.

The tear film layers 40, 42 are distributed across the corneal surface 22 and/or the convex surface 824 by motion of the eyelids 30, 32. For example, the eyelids 30, 32 raise and lower, respectively, to spread a small volume of tear film across the corneal surface 22 and/or the convex surface 824 of the eye-mountable device 810. The tear film layer 40 on the corneal surface 22 also facilitates mounting the eye-mountable device 810 by capillary forces between the concave surface 826 and the corneal surface 22. In some embodiments, the eye-mountable device 210 can also be held over the eye in part by vacuum forces against corneal surface 22 due to the concave curvature of the eye-facing concave surface 826.

As shown in the cross-sectional views in FIGS. 8c and 8d, the substrate 830 can be inclined such that the flat mounting surfaces of the substrate 830 are approximately parallel to the adjacent portion of the convex surface 824. As described above, the substrate 830 is a flattened ring with an inward-facing surface 832 (facing the concave surface 826 of the polymeric material 820) and an outward-facing surface 834 (facing the convex surface 824). The substrate 830 can have electronic components and/or patterned conductive materials mounted to either or both mounting surfaces 832, 834.

As shown in FIG. 8d, the bio-interactive electronics 860, controller 850, and conductive interconnect 851 are mounted on the outward-facing surface 834 such that the bio-interactive electronics 860 are facing the convex surface 824. As described above, the polymer layer defining the anterior side may be less than 50 micrometers thick, whereas the polymer layer defining the posterior side may be thicker. Thus, the bio-interactive electronics 860 may be less than 50 micrometers away from the convex surface 824 and may be a greater distance away from the concave surface 826. However, in other examples, the bio-interactive electronics 860 may be mounted on the inward-facing surface 832 of the substrate 830 such that the bio-interactive electronics 860 are facing the concave surface 826. The bio-interactive electronics 860 could also be positioned closer to the concave surface 826 than the convex surface 824.

IV. CONCLUSION

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method for fabricating an eye-mountable device, the method comprising:
   forming a first polymer layer;
   positioning a sensor apparatus on the first polymer layer, wherein the sensor apparatus comprises a support and an electrochemical sensor and a loop antenna mounted on the support, and wherein the sensor apparatus has a maximum height of between 50 micrometers and 150 micrometers; and
   forming a second polymer layer over the first polymer layer and the sensor apparatus, such that the sensor apparatus is fully enclosed by the first polymer layer and the second polymer layer, wherein one of the first polymer layer or the second polymer layer defines an anterior side of the eye-mountable device, and wherein the support is more rigid than the first and second polymer layers.

2. The method of claim 1, wherein the polymer layer defining the anterior side of the eye-mountable device has a thickness of less than 50 micrometers.

3. The method of claim 1, wherein the first and second polymer layers comprise a hydrogel material or a silicone elastomer.

4. The method of claim 1, wherein forming the first polymer layer comprises partially curing the first polymer layer to a partially-cured state, wherein the first polymer layer in the partially-cured state has a tackiness that facilitates adhesion thereto.

5. The method of claim 4, wherein positioning the sensor apparatus on the first polymer layer comprises positioning the sensor apparatus on the first polymer layer in the partially-cured state.

6. The method of claim 1, wherein the first and second polymer layers are transparent.

7. The method of claim 1, wherein the eye-mountable device has a maximum thickness that is between 100 micrometers and 500 micrometers.

8. The method of claim 1, wherein the first polymer layer comprises at least one interlocking feature,
wherein positioning the sensor apparatus on the first polymer layer comprises aligning the sensor apparatus with the at least one interlocking feature on the first polymer layer,
and wherein the second polymer layer comprises at least one corresponding interlocking feature, wherein each corresponding interlocking feature of the second polymer layer corresponds with a respective interlocking feature of the first polymer layer.

9. The method of claim 1, wherein forming the first polymer layer comprises forming the first polymer layer via spin-casting.

10. The method of claim 1, wherein forming the first polymer layer comprises forming the first polymer layer in a molding cavity.

11. A method comprising:
forming a first polymer layer, wherein the first polymer layer defines an anterior side of an eye-mountable device, and wherein the first polymer layer comprises at least one interlocking feature;
positioning a sensor apparatus on the first polymer layer, wherein the sensor apparatus comprises a support and an electrochemical sensor and a loop antenna mounted on the support, and wherein the sensor apparatus has a maximum height of between 50 micrometers and 150 micrometers; and
forming a second polymer layer, wherein the second polymer layer defines a posterior side of the eye-mountable device, and wherein the second polymer layer comprises at least one corresponding interlocking feature, wherein each corresponding interlocking feature corresponds with a respective interlocking feature of the first polymer layer, and wherein the support is more rigid than the first and second polymer layers.

12. The method of claim 11, wherein the at least one interlocking feature comprises a protrusion.

13. The method of claim 11, wherein a thickness of the first polymer layer, aside from the at least one interlocking feature, is less than 50 micrometers.

14. An eye-mountable device comprising:
a first polymer layer, wherein the first polymer layer defines an anterior side of the eye-mountable device, and wherein the first polymer layer comprises at least one interlocking feature;
a second polymer layer wherein the second polymer layer defines a posterior side of the eye-mountable device, and wherein the second polymer layer comprises at least one corresponding interlocking feature, wherein each corresponding interlocking feature corresponds with a respective interlocking feature of the first polymer layer; and
a sensor apparatus attached to at least one of the first polymer layer or the second polymer layer, wherein the sensor apparatus comprises a support and an electrochemical sensor and a loop antenna mounted on the support, wherein the sensor apparatus has a maximum height of between 50 micrometers and 150 micrometers, and wherein the support is more rigid than the first and second polymer layers.

15. The eye-mountable device of claim 14, wherein the first polymer layer has a thickness of less than 50 micrometers.

* * * * *